US009311825B2

(12) United States Patent
Lusted et al.

(10) Patent No.: US 9,311,825 B2
(45) Date of Patent: Apr. 12, 2016

(54) BIOMETRIC SENSING AND PROCESSING APPARATUS FOR MOBILE GAMING, EDUCATION, AND WELLNESS APPLICATIONS

(71) Applicant: SENSTREAM, INC., San Francisco, CA (US)

(72) Inventors: Hugh S. Lusted, Oregon House, CA (US); Ben Knapp, Blacksburg, VA (US); Jashojit Roy, San Francisco, CA (US)

(73) Assignee: SENSTREAM, INC., San Francisco, CA (US)

( * ) Notice: Subject to any disclaimer, the term of this patent is extended or adjusted under 35 U.S.C. 154(b) by 665 days.

(21) Appl. No.: 13/725,777

(22) Filed: Dec. 21, 2012

(65) Prior Publication Data

US 2013/0183646 A1    Jul. 18, 2013

Related U.S. Application Data

(60) Provisional application No. 61/630,877, filed on Dec. 22, 2011, provisional application No. 61/630,876, filed on Dec. 22, 2011.

(51) Int. Cl.
*G09B 19/00* (2006.01)
*A61B 5/16* (2006.01)
*A61B 5/00* (2006.01)

(52) U.S. Cl.
CPC ............... *G09B 19/00* (2013.01); *A61B 5/164* (2013.01); *A61B 5/6801* (2013.01); *A61B 5/6826* (2013.01)

(58) Field of Classification Search
CPC ............ A61M 2205/3592; A61B 5/68; A61B 5/6801; A61B 5/6825; A61B 5/6826; A61B 5/721; A61B 2562/0219; A61B 5/165
See application file for complete search history.

(56) References Cited

U.S. PATENT DOCUMENTS

| 2,339,579 A | 1/1944 | Milne et al. |
| 3,556,083 A | 1/1971 | Grichnik et al. |
| 3,727,604 A | 4/1973 | Sidwell et al. |
| 3,841,316 A | 10/1974 | Meyer |

(Continued)

OTHER PUBLICATIONS

Jaimovich, J., et al. "Emotion in Motion: A Study of Music and Affective Response," 9th International Symposium on Computer Music Modelling and Retrieval (CMMR 2012) Jun. 19-22, 2012, pp. 1-16.

(Continued)

*Primary Examiner* — Catherine Voorhees
(74) *Attorney, Agent, or Firm* — O'Banion & Ritchey LLP; John P. O'Banion

(57) ABSTRACT

An apparatus for interoperably utilizing multiple biosensor data obtained from a finger of the user. A biometric sensor board is retained in a housing adapted for retaining a finger of the user and maintaining multiple sensors in contact with the skin thereof. Implementations are described for fingertip and ring mounted sensor boards. In one implementation, these sensors can be sensors electrodermal response (EDR), or photoplethysmograph (PPG) signals, or temperature, or acceleration in three axes, and combinations thereof. The biometric sensor board registers and processes the signals from the sensors and communicates them to a mobile device which interoperably utilizes multiple sensor information to determine aspects of user emotional state within an application to generate results which are displayed on the mobile device.

26 Claims, 10 Drawing Sheets

(56) References Cited

U.S. PATENT DOCUMENTS

| | | |
|---|---|---|
| 3,870,034 A | 3/1975 | James |
| 4,015,595 A | 4/1977 | Benjamin, Jr. |
| 4,088,125 A | 5/1978 | Forgione et al. |
| 4,100,536 A | 7/1978 | Ball et al. |
| 4,149,716 A | 4/1979 | Scudder |
| 4,183,360 A | 1/1980 | Carlson et al. |
| 4,246,906 A | 1/1981 | Winberg et al. |
| 4,358,118 A | 11/1982 | Plapp |
| 4,461,301 A | 7/1984 | Ochs |
| 4,632,126 A | 12/1986 | Aguilar |
| 4,683,891 A | 8/1987 | Cornellier et al. |
| 4,690,142 A | 9/1987 | Ross et al. |
| 5,016,213 A | 5/1991 | Dilts et al. |
| 5,243,517 A | 9/1993 | Schmidt et al. |
| 5,253,168 A | 10/1993 | Berg |
| 5,364,107 A | 11/1994 | Kinkead |
| 5,507,291 A | 4/1996 | Stirbl et al. |
| 5,544,661 A | 8/1996 | Davis et al. |
| 5,577,510 A | 11/1996 | Chittum et al. |
| 5,676,138 A | 10/1997 | Zawilinski |
| 5,718,235 A | 2/1998 | Golosarsky et al. |
| 5,720,619 A | 2/1998 | Fisslinger |
| 5,725,472 A | 3/1998 | Weathers |
| 5,741,217 A | 4/1998 | Gero |
| 5,791,347 A | 8/1998 | Flaherty et al. |
| 5,860,935 A | 1/1999 | Blaszynski et al. |
| 5,891,044 A | 4/1999 | Golosarsky et al. |
| 5,987,415 A | 11/1999 | Breese et al. |
| 5,990,866 A | 11/1999 | Yollin |
| 6,024,700 A | 2/2000 | Nemirovski et al. |
| 6,185,534 B1 | 2/2001 | Breese et al. |
| 6,190,314 B1 | 2/2001 | Ark et al. |
| 6,305,943 B1 | 10/2001 | Pougatchev et al. |
| 6,309,342 B1 | 10/2001 | Blazey et al. |
| 6,358,201 B1 | 3/2002 | Childre et al. |
| 6,402,690 B1 | 6/2002 | Rhee et al. |
| 6,413,223 B1 | 7/2002 | Yang et al. |
| 6,415,176 B1 | 7/2002 | Scheirer et al. |
| 6,422,999 B1 | 7/2002 | Hill |
| 6,453,194 B1 | 9/2002 | Hill |
| 6,478,735 B1 | 11/2002 | Pope et al. |
| 6,487,442 B1 | 11/2002 | Wood |
| 6,520,905 B1 | 2/2003 | Surve et al. |
| 6,527,711 B1 | 3/2003 | Stivoric et al. |
| 6,589,171 B2 | 7/2003 | Keirsbilck |
| 6,605,038 B1 | 8/2003 | Teller et al. |
| 6,616,613 B1 | 9/2003 | Goodman |
| 6,656,116 B2 | 12/2003 | Kim et al. |
| 6,721,706 B1 | 4/2004 | Strubbe et al. |
| 6,728,679 B1 | 4/2004 | Strubbe et al. |
| 6,731,307 B1 | 5/2004 | Strubbe et al. |
| 6,754,524 B2 | 6/2004 | Johnson, Jr. |
| 6,757,559 B2 | 6/2004 | Cohen |
| 6,795,808 B1 | 9/2004 | Strubbe et al. |
| 6,820,037 B2 | 11/2004 | Simon |
| 6,905,470 B2 | 6/2005 | Lee et al. |
| 6,990,426 B2 | 1/2006 | Yoon et al. |
| 6,997,879 B1 | 2/2006 | Turcott |
| 7,020,508 B2 | 3/2006 | Stivoric et al. |
| 7,079,888 B2 | 7/2006 | Oung et al. |
| 7,117,032 B2 | 10/2006 | Childre et al. |
| 7,150,715 B2 | 12/2006 | Collura et al. |
| 7,153,262 B2 | 12/2006 | Stivoric et al. |
| 7,163,512 B1 | 1/2007 | Childre et al. |
| 7,181,693 B1 | 2/2007 | Anderson et al. |
| 7,213,600 B2 | 5/2007 | El-Nokaly et al. |
| 7,215,987 B1 | 5/2007 | Sterling et al. |
| 7,257,438 B2 | 8/2007 | Kinast |
| 7,261,690 B2 | 8/2007 | Teller et al. |
| 7,271,809 B2 | 9/2007 | Fedorovskaya et al. |
| 7,278,975 B2 | 10/2007 | McCamish et al. |
| 7,285,090 B2 | 10/2007 | Stivoric et al. |
| 7,333,969 B2 | 2/2008 | Lee et al. |
| 7,438,688 B2 | 10/2008 | Kobayashi et al. |
| 7,481,537 B2 | 1/2009 | Meadows |
| 7,481,772 B2 | 1/2009 | Banet |
| 7,502,643 B2 | 3/2009 | Farringdon et al. |
| 7,529,579 B2 | 5/2009 | Colombo et al. |
| 7,543,330 B2 | 6/2009 | Garbow et al. |
| 7,547,279 B2 | 6/2009 | Kim et al. |
| 7,602,301 B1* | 10/2009 | Stirling .............. A61B 5/1127 340/573.1 |
| 7,650,177 B2 | 1/2010 | Hoarau et al. |
| 7,658,716 B2 | 2/2010 | Banet et al. |
| 7,674,230 B2 | 3/2010 | Reisfeld |
| 7,689,437 B1 | 3/2010 | Teller et al. |
| 7,691,049 B2 | 4/2010 | Wood et al. |
| 7,729,733 B2 | 6/2010 | Al-Ali et al. |
| 7,751,878 B1 | 7/2010 | Merkle et al. |
| 7,761,128 B2 | 7/2010 | Al-Ali et al. |
| 7,774,052 B2 | 8/2010 | Burton et al. |
| 7,794,406 B2 | 9/2010 | Reisfeld et al. |
| 7,815,582 B2 | 10/2010 | Imboden et al. |
| 7,889,073 B2 | 2/2011 | Zalewski |
| 7,891,355 B2 | 2/2011 | Al-Ali et al. |
| 7,894,868 B2 | 2/2011 | Al-Ali et al. |
| 7,899,507 B2 | 3/2011 | Al-Ali et al. |
| 7,914,468 B2 | 3/2011 | Shalon et al. |
| 7,918,780 B2 | 4/2011 | El-Nokaly et al. |
| 7,938,789 B2 | 5/2011 | Imboden et al. |
| 7,955,259 B2 | 6/2011 | Lee et al. |
| 8,002,711 B2 | 8/2011 | Wood et al. |
| 8,033,996 B2 | 10/2011 | Behar |
| 8,066,637 B2 | 11/2011 | Childre et al. |
| 8,073,631 B2 | 12/2011 | Wilber et al. |
| 8,073,707 B2 | 12/2011 | Teller et al. |
| 8,125,314 B2 | 2/2012 | Fithian et al. |
| 8,132,229 B2 | 3/2012 | Garbow et al. |
| 8,155,733 B2 | 4/2012 | Nng |
| 8,157,729 B2 | 4/2012 | Yang et al. |
| 8,157,731 B2 | 4/2012 | Teller et al. |
| 8,160,918 B1 | 4/2012 | Blair et al. |
| 8,180,638 B2 | 5/2012 | Kim et al. |
| 8,190,223 B2 | 5/2012 | Al-Ali et al. |
| 8,197,415 B2 | 6/2012 | Rosch et al. |
| 8,224,411 B2 | 7/2012 | Al-Ali et al. |
| 8,251,912 B2 | 8/2012 | Shelley et al. |
| 8,255,028 B2 | 8/2012 | Al-Ali et al. |
| 8,271,077 B1 | 9/2012 | Rotenberg |
| 8,285,352 B2 | 10/2012 | Addison et al. |
| 8,296,172 B2 | 10/2012 | Marci et al. |
| 8,298,154 B2 | 10/2012 | Hete et al. |
| 8,308,562 B2 | 11/2012 | Patton |
| 8,321,004 B2 | 11/2012 | Moon et al. |
| 8,332,017 B2 | 12/2012 | Tarassenko et al. |
| 2008/0208016 A1* | 8/2008 | Hughes .............. A61B 5/0533 600/301 |
| 2008/0214903 A1* | 9/2008 | Orbach .............. G06Q 50/22 600/301 |
| 2009/0318779 A1* | 12/2009 | Tran .............. A61B 8/565 600/301 |
| 2010/0217100 A1* | 8/2010 | LeBoeuf .............. A61B 5/00 600/301 |
| 2011/0009754 A1* | 1/2011 | Wenzel .............. A61B 5/0215 600/485 |
| 2012/0329432 A1* | 12/2012 | Gupta .............. G06Q 30/02 455/414.1 |
| 2013/0116514 A1* | 5/2013 | Kroner .............. A61B 7/00 600/301 |

OTHER PUBLICATIONS

Jaimovich, J., et al. "The Emotion in Motion Experiment: Using an Interactive Installation as a Means for Understanding Emotional Response to Music," Proceedings of the New Interfaces for Musical Expression Conference, Ann Arbor, Michigan, May 2012, pp. 1-2.

Gabrielsson and Juslin, "Emotional Expression in Music Performance: Between the Performer's Intention and the Listener's Experience," Psychology of Music and Music Education, 1996, vol. 24, pp. 68-91.

BioEmo Version 1.1, Apr. 2009, product webpage, http://infusionsystems.com/catalog/product_info.php/products_id/203, retrieved Sep. 2, 2013, 1-3.

(56) References Cited

OTHER PUBLICATIONS

R. B. Knapp and B. Bortz, "MobileMuse: Integral Music Control Goes Mobile," Proceedings of the New Interfaces for Musical Expression Conference, Oslo, Norway, Jun. 2011, pp. 1-4.

J. Jaimovich and R. B. Knapp, "Synchronization of Multimodal Recordings for Musical Performance Research," Proceedings of the New Interfaces for Musical Expression Conference, Sydney, Australia, Jun. 2010, pp. 1-3.

Affectiva Q sensor, user manual, www.affectiva.com/q-sensor, retrieved on Sep. 30, 2013, pp. 1-66.

Jaimovich, et al., "Contagion of Physiological Correlates of Emotion between Performer and Audience: An Exploratory Study," Proceedings of the International Conference on Bio-inspired Systems and Signal Processing, Valencia, Spain, Jan. 2010, pp. 1-8.

Coghlan, et al., "AffecTech—an Affect-aware Interactive AV Artwork," Proceedings of the International Society of Electronic Arts (ISEA) Conference, Aug. 2009, pp. 1-6.

N. Coghlan and R. B. Knapp, "'Inner-Active Art: An Examination of Aesthetic and Communicative Issues in Physiologically Based Artworks," Proceedings of the International Society of Electronic Arts (ISEA) Conference, Aug. 2009, pp. 1-7.

Knapp, et al., "Techniques for Gesture Measurement in Musical Performance," in Proceedings of the 2008 Conference on New Interfaces for Musical Expression, Genova, Italy, 2008, pp. 423-424.

N. Coghlan and R. B. Knapp, "Sensory Chairs: A System for Biosignal Research and Performance," Proceedings of the New Interfaces for Musical Expression 2008 Conference, Genoa, Italy, Jun. 5-8, 2008, pp. 1-4.

* cited by examiner

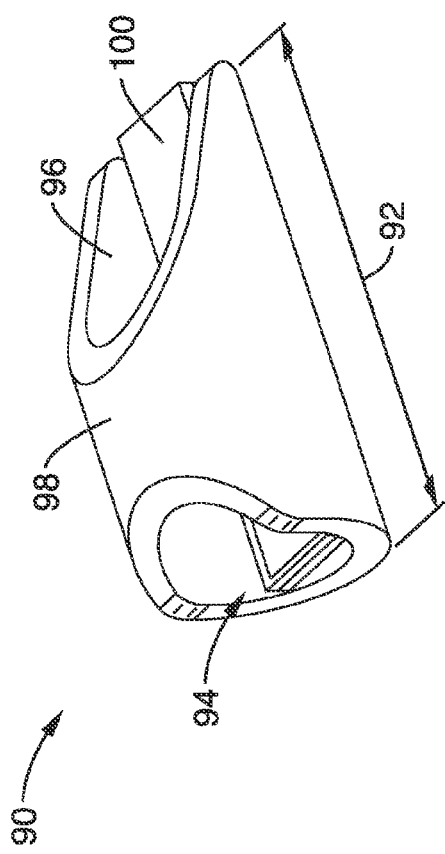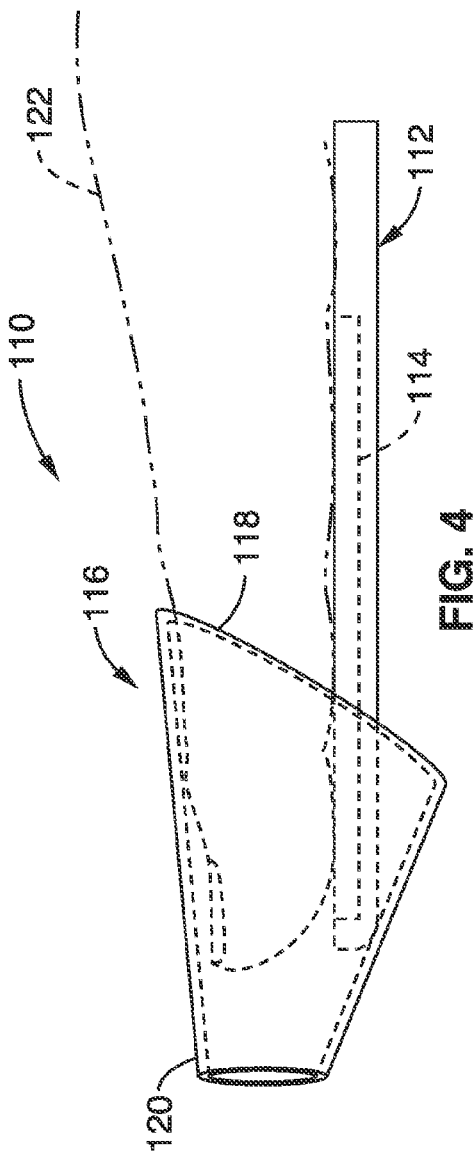

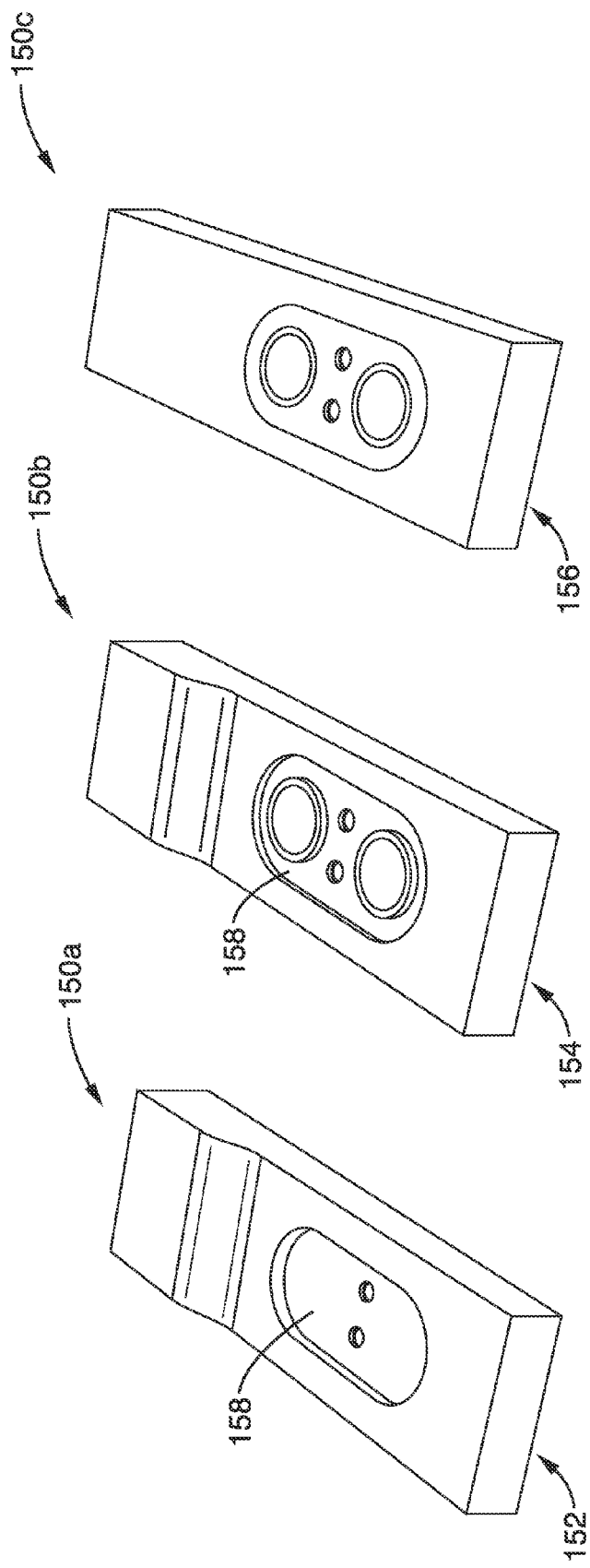

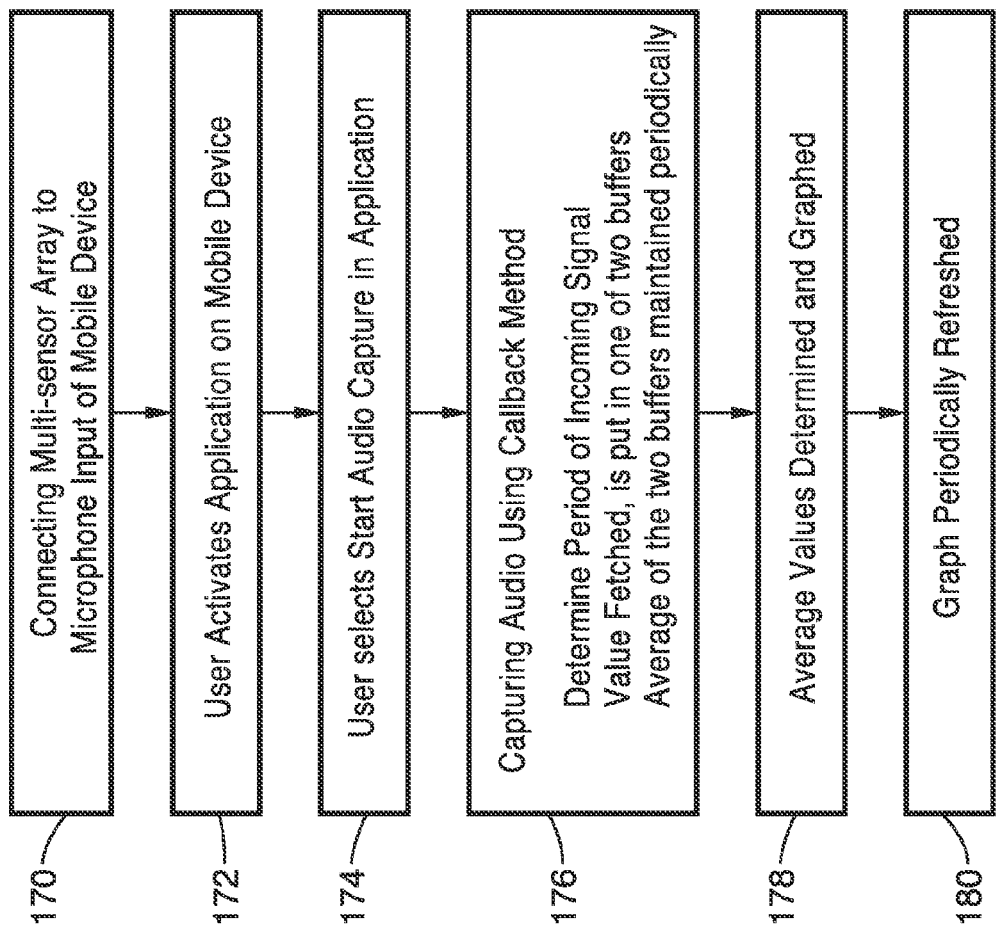

BIOMETRIC SENSING AND PROCESSING APPARATUS FOR MOBILE GAMING, EDUCATION, AND WELLNESS APPLICATIONS

CROSS-REFERENCE TO RELATED APPLICATIONS

This application is a nonprovisional of U.S. provisional patent application Ser. No. 61/630,876 filed on Dec. 22, 2011, incorporated herein by reference in its entirety, and is a nonprovisional of and U.S. provisional patent application Ser. No. 61/630,877 filed on Dec. 22, 2011, incorporated herein by reference in its entirety.

STATEMENT REGARDING FEDERALLY SPONSORED RESEARCH OR DEVELOPMENT

Not Applicable

INCORPORATION-BY-REFERENCE OF MATERIAL SUBMITTED ON A COMPACT DISC

Not Applicable

NOTICE OF MATERIAL SUBJECT TO COPYRIGHT PROTECTION

A portion of the material in this patent document is subject to copyright protection under the copyright laws of the United States and of other countries. The owner of the copyright rights has no objection to the facsimile reproduction by anyone of the patent document or the patent disclosure, as it appears in the United States Patent and Trademark Office publicly available file or records, but otherwise reserves all copyright rights whatsoever. The copyright owner does not hereby waive any of its rights to have this patent document maintained in secrecy, including without limitation its rights pursuant to 37 C.F.R. §1.14.

BACKGROUND OF THE INVENTION

1. Field of the Invention

This invention pertains generally to biofeedback devices, and more particularly to an biometric sensing device interacting with a mobile platform configured for executing emotion sensing enabled software applications.

2. Description of Related Art

Various forms of electronic biofeedback have long been available. Typically, these devices are configured for fulfilling a very specific and narrow role. For example, the electrodermal response (EDR) was first measured by the psycho-galvanometer, as it was called to measure skin resistance. The EDR device is best known as one element of a police style lie-detector. Some biofeedback devices today utilize the same circuitry and electrodes as utilized when this device was developed four decades ago. The electrodermal response is the medically preferred term for galvanic skin response (GSR). Another specific device is the photoplethysmograph (PPG), which is well known in hospitals for quick assessment of heart rate based on sensing at the fingertip.

However, these devices are generally directed to specific purposes and not generally applicable to interoperate with mobile platforms executing internet based applications utilizing multiple biofeedback resources.

BRIEF SUMMARY OF THE INVENTION

The invention provides for placement of multiple sensors on the finger, whereby the combination of sensor data allows for deriving accurate assessments of the physiological and emotional state of the user within applications executing on the mobile device. It should be recognized that the present invention only requires that application software be loaded on a general purpose mobile device, no additional hardware or hardware changes are required on the mobile device side. Thus, a user need only obtain the biometric sensor device for attachment to their mobile device, and a desired application to execute from that mobile device.

The invention incorporates a plurality of sensor types, exemplified herein with four sensor types, into a package wearable on any finger of a user's hand. In the current embodiment, the sensors and associated hardware are contained on a board that can be worn on a finger in various ways, such as over a fingertip (e.g., 2.5 inch) or in a smaller package (e.g., 0.75 inch) that can be worn like a ring.

According to at least one embodiment of the invention, the biometric sensor incorporates the following. (1) EDR (electrodermal response) for measuring user arousal and relaxation, with phasic sensing (fast arousal) and tonic sensing (longer response time—like mood) being derived from this sensor. (2) PPG (photoplethysmograph) for measuring user cardiac pulse, with heart rate (HR) and heart rate variability (HRV) being derived from PPG sensor data. (3) A temperature sensor (e.g., thermistor) for measuring skin temperature. (4) A 3-D accelerometer sensor incorporated into the device to sense accelerations in three spatial dimensions in response to user finger movement.

In at least one embodiment of the device, the biometric sensor device of the invention is inserted into the audio microphone jack of a smart phone or other mobile device, and interacts with a software application on the device. The software application provides functionality (e.g., games, educational, and/or health) for a single user or for multiple users which interact together in scenarios through the Internet.

Further aspects of the invention will be brought out in the following portions of the specification, wherein the detailed description is for the purpose of fully disclosing preferred embodiments of the invention without placing limitations thereon.

BRIEF DESCRIPTION OF THE SEVERAL VIEWS OF THE DRAWING(S)

The invention will be more fully understood by reference to the following drawings which are for illustrative purposes only:

FIG. 3 is a rendition of a biometric sensor array housing with circuit board installed, according to an embodiment of the present invention.

FIG. 4 is a cross-section view of a biometric sensor array housing, using elastic cone fingertip retention, according to an embodiment of the present invention.

FIG. 8A through FIG. 8C are renditions of alternate dual contact embodiments for the biometric sensor array, according to embodiments of the present invention.

FIG. 11 is a flowchart connecting the biometric sensor array to a mobile device using the audio port and collecting biofeedback data.

DETAILED DESCRIPTION OF THE INVENTION

1. Hardware Description

1.1 Introduction

Hardware of at least one embodiment of the biometric sensor array comprises four principal sections. (A) A biometric sensor circuit and board including sensor elements, processor hardware, and firmware code for execution on the processor. (B) A signal interface connecting the sensor board with the mobile device to facilitate data transfer. By way of example and not limitation, the current embodiment provides a signal interface using a multichannel audio frequency electronic signal (e.g., generated by an amplitude modulation program executing on the processor) that connects to an audio microphone input of a mobile device. Other embodiments of the present invention are configured with a wireless signal interface, such as a Bluetooth interface or similar digital communication mechanism of the mobile device. (C) A physical housing which retains the finger in proper sensing position on the board and also houses the circuit board. (D) A software interface within one or more applications containing programming executable on the mobile device (e.g., smart phone or any mobile device. One of ordinary skill in the art will appreciate that the functions of the present invention may be divided in countless ways using any number of module naming schemes and various electronic implementations without departing from the teachings of the present invention.

1.2 Example Embodiment

Figure 1A:
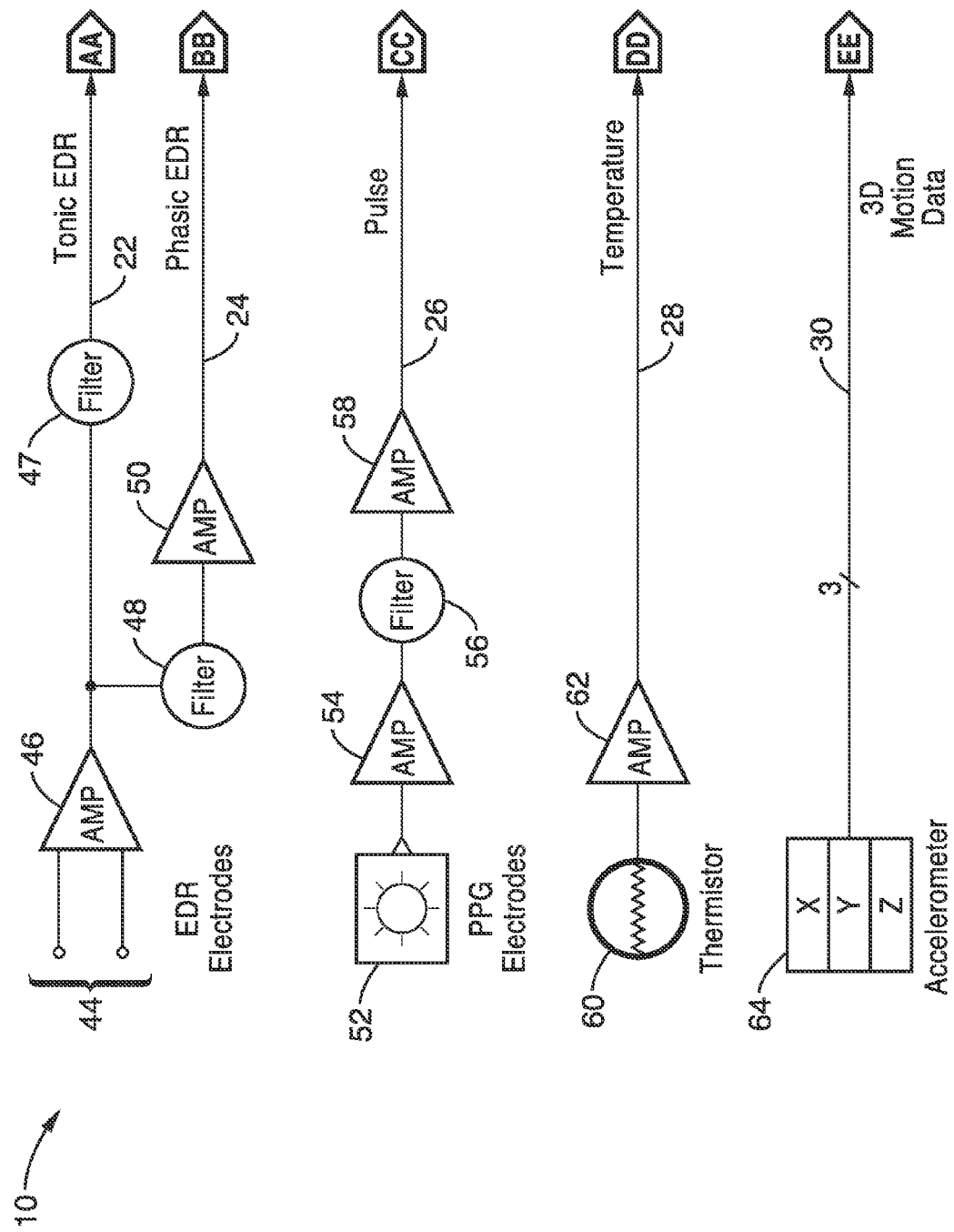
FIG. 1A and FIG. 1B is a block diagram of the biometric sensor array device according to an embodiment of the present invention.
Figure 1B:
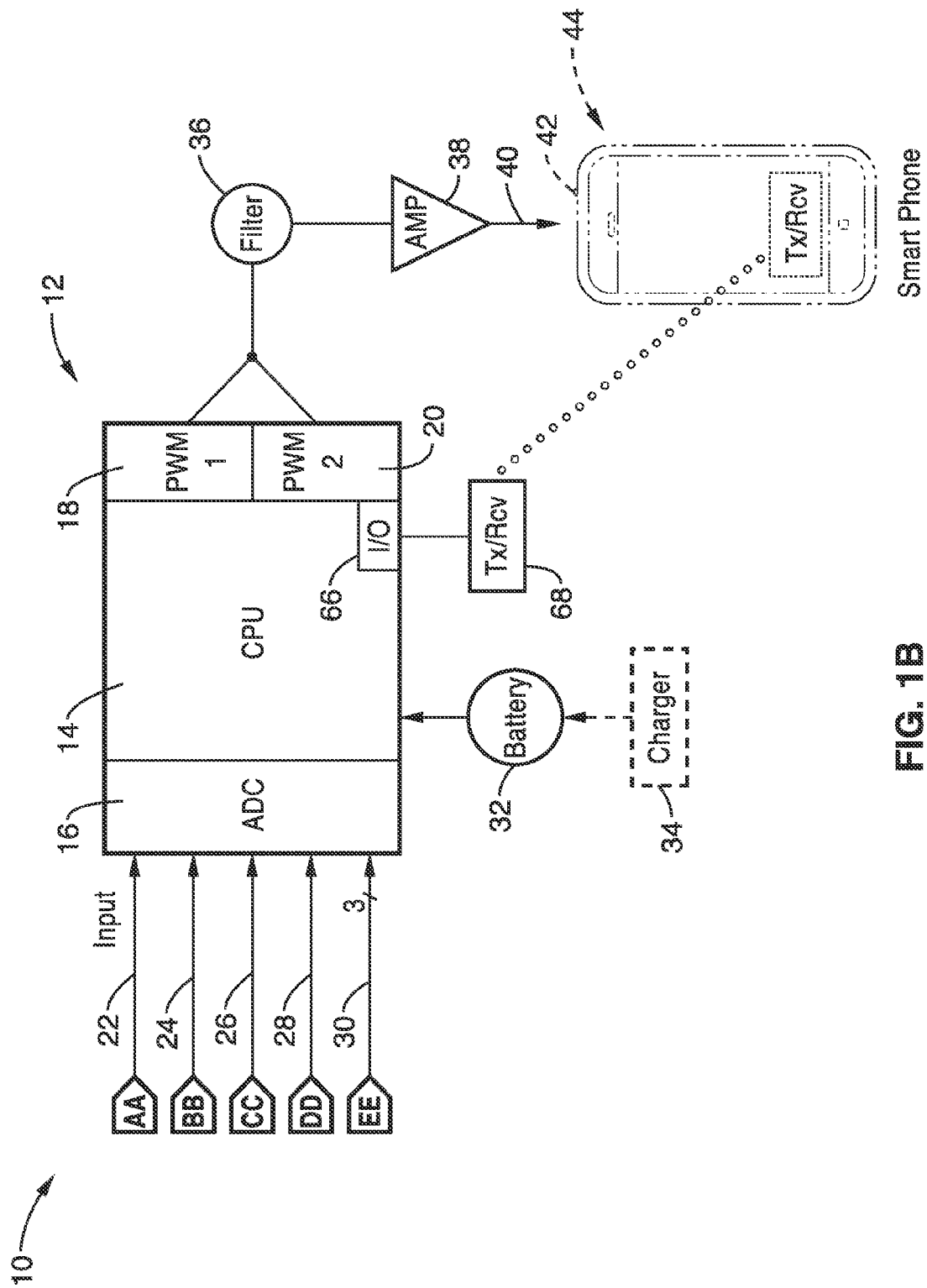

FIG. 1A and FIG. 1B illustrate a block diagram of the biometric sensor device according to an example embodiment 10. A control block 12, is shown exemplified as a microcontroller containing a processor 14 (CPU and memory) and incorporating conversion functions for analog-to-digital conversion (ADC) 16 of analog inputs 22, 24, 26, 28, 30, and pulse-width modulation (PWM) of outputs 18, 20. It will be seen that control block 12 converts analog sensor signals to digital information, and executes programming from memory to process those signals and is configured to communicate data associated with those signals to a mobile device. It will be recognized that a wide variety of processing elements with internal or external conversion elements may be substituted for control block 12 of the present device without departing from the teachings of the present invention.

A battery 32 and optional charger circuit 34 are shown for supplying power to the control block 12. The power source may alternatively comprise any desired means of powering the circuit, including but not limited to primary batteries (e.g., lithium or alkaline batteries, such as coin cells), rechargeable batteries (e.g., lithium, NiMH (nickel-metal-hydride), NiCad (nickel-cadmium), high capacity capacitors (e.g., dual-layer capacitors (DLCs), solar cells, or any other source of electrical power.

One implementation of the biometric sensor device utilizes an audio signal interface to connect to a microphone input of any mobile device. The processed input signals are amplitude modulated to audio frequency and then added together to enable multiple channels (frequency division multiplexed) to be transmitted over a single audio channel. PWM outputs 18, 20 are shown being output from control block 12 for communicating with the smart device through its microphone input. Pulse width modulated signals 18, 20 are filtered 36 and amplified 38 into an audio output 40 configured for connection, such as using an audio plug from the biometric sensor array device configured for connection into the microphone (mic) input 42 of a smart phone or other mobile device 44.

FIG. 1A and FIG. 1B also illustrate an alternative wireless connection between the biometric sensor and mobile device. At least one embodiment of the biometric sensor comprises a digital communication connection, such as through digital port 66 connected to a transmitter or transceiver (transmitter+ receiver) 68 configured for wirelessly communicating to the mobile device 44. A standard protocol, such as Bluetooth, is a beneficial choice as many mobile devices are already configured with Bluetooth connectivity, while it is a low power short distance interface. The advantage of the digital interface is high-speed and simultaneous multichannel capability beyond two channels. Eight channel data transfer is available with a Bluetooth interface which enables the full suite of sensor channels currently available on the biometric sensor board.

In FIG. 1A, analog circuits of four sensors elements are shown for sending input signals to the processor. The EDR uses two electrodes 44 that register changes in skin resistance, which is amplified 46 and low-pass filtered 47 to generate a tonic EDR signal voltage 22 sent to the processor analog-to-digital converter (ADC) input. It will be seen here that the EDR signal is divided into two different EDR channels: tonic and phasic. The tonic signal is a more slowly varying DC signal, while the phasic signal provides a faster response with user arousal and relaxation. Phasic information from amplifier 46 is high-pass filtered 48, and further amplified 50 to generate a phasic EDR signal voltage 24. The low frequency cutoff for the phasic signal is approximately 0.5 Hz, and for the slower tonic signal it is approximately 0.05 Hz.

The PPG sensor 52 in this implementation utilizes an infrared (IR) sensitive photo-transistor that produces a small voltage in response to IR illumination. Blood perfusion in the finger produced by cardiac pulses cause the IR light to be scattered and thus the output of the IR detector varies with each pulse. The IR signal from PPG sensor 52 is preferably amplified 54, filtered 56, and amplified again 58 before input to the processor as PPG signal 26.

The temperature sensor 60 is exemplified as a thermistor which is a resistive element whose resistance varies with changes in temperature. Output from temperature sensor 60 is amplified before input to the processor as a temperature signal 28.

The accelerometer 64 generates information on acceleration in each of its three sensing axes of X, Y and Z directions. In this particular implementation, the accelerometer package sends a time-varying voltage corresponding to each of the three axes of movement as 3D motion data 30 to the processor. For the sake of simplicity of illustration, the figure shows one signal line with the strike notation marked with a "3" indicating there are three signal paths. Accelerometers can be configured with various forms of output, for example various forms of analog output, frequency output, or digital output for connection to a parallel or serial input of the processor.

In the present invention, a significant purpose of the accelerometer is to allow the processor to perform the important function of motion artifact removal from the data received from the biometric sensor array. Motion can interfere with physiological signal measurements, and is mediated herein by acceleration data received from the finger sensor device in response to measuring triaxial motion. The acceleration sensor also allows the device to assess intentional motion of the user, for example walking, or other physical activity and is utilized in certain embodiments of the invention for correlating user activity to changes in heart rate and breathing. Still further, the acceleration sensing it utilized in certain application embodiments of the invention to receive specific forms of user input, such as in response to motion direction sensing and gesture recognition which are utilized in some existing applications.

One of ordinary skill in the art will recognize that there exists a large number of viable sensors having various forms of interface with a processor, and that the inventive system can be configured to utilize any of these without departing from the teachings of the present invention.

In at least one embodiment, converted signals are sent in real time from control block 12 to the mobile device. In the implementation shown in FIG. 1A and FIG. 1B, a two channel transmit path is supported to the mobile device whereby any two of the five sensor signals 22, 24, 26, 28 or 30 are simultaneously communicated (in two frequency division channels) to the mobile device. The processor utilizes pulse-width modulation (PWM) to generate two amplitude modulated audio carrier waves of different frequencies, with digitized and typically scaled, sensor input signals encoded in the amplitude of the carrier waves within the frequency division multiplexing. The use of only a two channel analog communications path in the present implementation reduces manufacturing cost while providing sufficiently rapid communication of sensor data to the mobile device. Although the processor is capable of encoding all five sensor inputs, the inexpensive processor chosen in the implementation shown limits the carriers to two due to processor efficiency. However, it should be appreciated that the processor may alternate between sending data from different combinations of sensor signals, such as in a round-robin manner, to provide a form of temporal multiplexing of any desired combination of the five sensor inputs. It will be also appreciated that the signals are not all subject to the same rate of change. For example, input from the temperature sensor is not subject to very rapid changes and thus, does not need to be communicated at the same rate as the other signals. Additionally, the EDR sensor is used to provide both phasic and the more slowly varying tonic signals.

1.3 Sensor Characteristics

This invention uses a temperature sensor on the finger as an input to be used in conjunction with the EDR to give an assessment of user mood. The finger vasculature warms and cools more rapidly than the hand and gives a faster "mood" response.

As with EDR, motion artifact is a problem with the PPG measurement, which is mitigated in the present invention in multiple ways. First, elements of biometric sensor design provide reliable contact which reduces relative motion between the sensors and the skin of the finger. It will be appreciated for example that the adjustable finger enclosure reduces the motion problem. Secondly, the sensors are co-located at the finger, wherein each is generally subject to the same motion. For example, the EDR and PPG sensors are collocated, whereby PPG data is derived from the same capillary bed as the data from the EDR sensor and provides data that is temporally aligned with the other sensor modes. Thirdly, the 3-axis accelerometer is used in combination with programming which utilizes acceleration data to compensate for any movement which arises. For example, the biometric sensor circuit uses the acceleration signals to interoperate with the other sensor signal types depending on the application being executed. For instance accelerometer data can be used to cancel motion artifacts from the EDR or PPG sensors in cases of extreme activity, while additionally the accelerometer can be utilized to enable a pointing function with appropriate finger motion, or other use of gesture as a user input.

1.4 Sensor Circuit Board and Finger Enclosure

A primary consideration on the circuit board layout is to assure proper positioning of the sensor elements together on the finger. In the current embodiment, the sensor elements are positioned on the axial surface of the fingertip.

Figure 2:
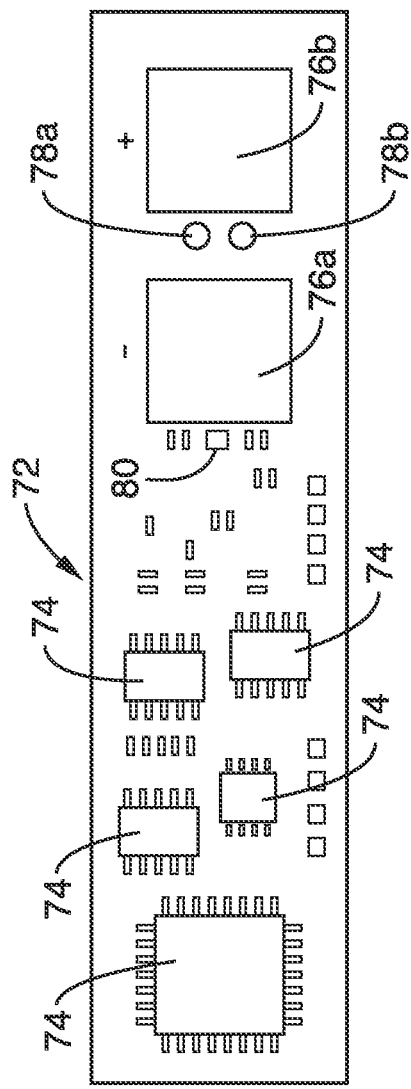
FIG. 2 is a rendition of a biometric sensor array circuit board according to an embodiment of the present invention.

FIG. 2 illustrates an example embodiment 10 of a biometric sensor circuit board showing the sensor element side 72 of the board with numerous integrated circuits 74 (including processor and accelerometer) and other electronic circuits. Two square EDR electrode contacts 76a, 76b are shown for being retained proximal to the finger surface. PPG sensor elements 78a, 78b, considered by way of example in this embodiment as an IR emitter and receiver, are shown positioned between the square EDR electrode contacts. A temperature sensor 80 is also seen in the figure as the small component directly to the left of the left EDR contact 76a.

The finger enclosure retains the finger in functional contact with the sensor elements which is a critical aspect of the biometric sensor embodiments. A couple of important elements to the enclosure structures are as follows. (1) A design that maintains light contact pressure on fingers of different sizes (including five fingers per hand, adult male and female, children) whereby the enclosure assures proper finger to sensor contact under moderate use conditions. (2) An EDR sensor design providing an electrode surface geometry that minimizes electrode to skin motion artifacts and improves electrode to skin contact. In at least one embodiment of the invention, the finger contacts are so shaped as to create a partial vacuum (PV) between the electrode surface and the skin, thus stabilizing the electrode to skin interface.

FIG. 3 illustrates an example embodiment 90 of an enclosure design for the biometric sensor device. In this embodiment, the enclosure comprises a tube-like structure having a tapered interior, and preferably significantly larger (e.g., approximately 50% more) finger contact surface on the interior side of the finger rather than on the exterior (knuckle) side of the finger. The length of the housing 92, is approximately 2½ inches in length with a proximal opening diameter 94 of approximately ¾ inch. The embodiment shown can accommodate a range of finger sizes, while it may be too large for children and too small for large adults. It will be appreciated that the dimensions of the housing can be changed to suit different sized individuals (e.g., small, medium and large) without departing from the teachings of the invention. Distal opening 96 is shown having a smaller diameter than the proximal end opening 94, and in alternate embodiments (e.g., FIG. 4) the distal end may contain a flexible conical structure to assure proper finger contact with the multiple sensor (e.g., EDR and PPG). It can be seen in the figure that the enclosure is configured with a first side 92 length that is significantly longer that the second side 98. The second side is configured far enough toward the proximal end (opening 94) to slide over, or past the first knuckle (closest the fingertip), to limit movement of the fingertip relative to the sensors. The biometric sensor circuit board 100, seen in FIG. 2, is shown mounted interior the enclosure for receivable contact with the interior side of the finger and maintaining sensors in proper alignment with the fingertip pad (as opposed to the fingernail on its opposite side of the finger). As the user advances the finger into the enclosure, the finger tip is put in a light pressure contact with the sensor board. The enclosure 90 is preferably fabricated from plastic (e.g., polyvinyl chloride (PVC)), although other materials (preferably non-conductive) may be utilized.

FIG. 4 illustrates an example embodiment 110 utilizing a "tray" shaped enclosure for the sensor board 114 on a tapered enclosure 112. An elastic cone 116 is shown on the distal end of the enclosure 112 configured for retaining a finger 122. The elastic cone 116 comprises a proximal opening 118 and distal end opening 120. In at least one embodiment, a series of elastic cones are provided and the user can choose a size that fits over the top of the finger and under the nose of the enclosure. As the elastic is advanced back toward the knuckle the increasing diameter of the enclosure tightens the elastic around the finger and secures the sensor board against the finger tip. The advantage of this design is that all finger sizes can be accommodated with elastic cones of different diameters. Flexible cones may be constructed in various ways, such as formed from 0.75 inch wide elastic band stock, or molded of an elastomeric material. For example, using elastic band stock, elastic pieces may be cut in sections ranging from 2 inches long to 4 inches long in 0.50 increments, yielding 8 different lengths. Each section is rolled into a loop with one end turned at a 45 degree angle so the resulting loop has a small and large diameter opening. Other finger enclosures using various materials may be implemented to fulfill the requirements of providing a secure finger to board contact while accommodating any desired range of finger sizes.

Figure 6:
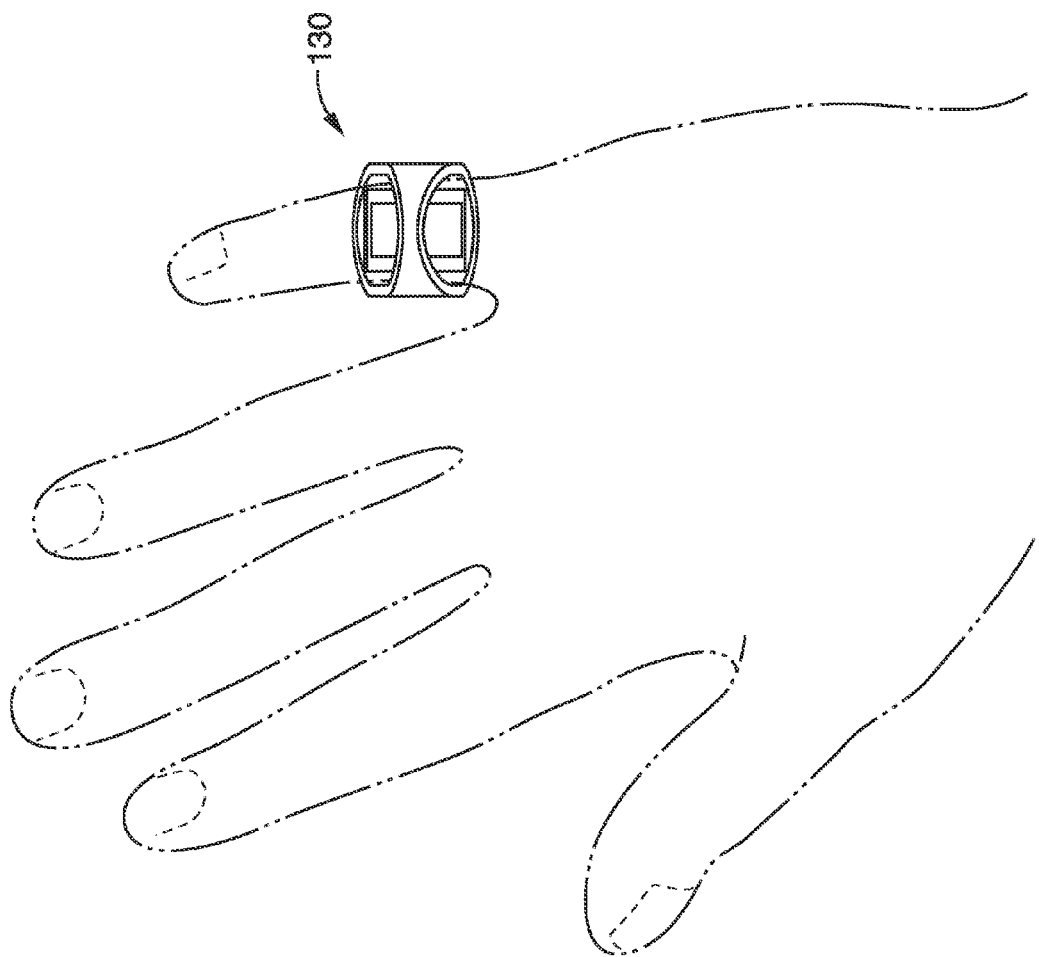
FIG. 6 is a rendition of the biometric sensor array ring housing of FIG. 5, shown being worn by a user as a ring.
Figure 5:
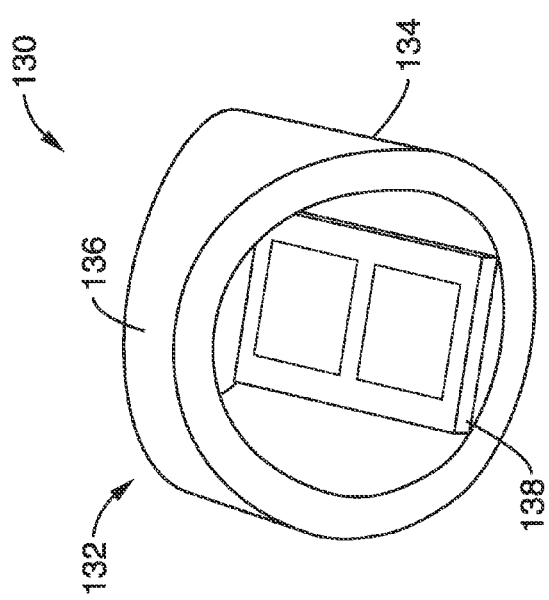
FIG. 5 is a rendition of a biometric sensor array ring housing with circuit board installed, according to an embodiment of the present invention.

FIG. 5 and FIG. 6 illustrates another example embodiment 130 of a biometric sensor board being incorporated into a ring design. The ring itself with attached sensor board 138 is shown in FIG. 5, while the ring is shown worn on a finger of the user in FIG. 6. This design has been reduced to practice using a ring worn in the standard position on the third phalange of the finger. As can be seen in the figure, the ring has a housing portion 132 with lower portion 134 and upper portion 136. Similar to the embodiment of FIG. 4, the lower body 134 is more elongate than the upper body portion 136. A biometric sensor circuit board 138 is seen retained in the ring embodiment. The data provided by the EDR, PPG, temperature sensor, and accelerometer are all substantially equivalent to the data obtained from the fingertip (first phalange). The ring design as shown has limited space available for the battery, however, it will be appreciated that different battery configurations can be utilized to accommodate the ring (e.g., smaller batteries, multiple batteries in parallel, battery within, or as external elements (e.g., a "stone" of the ring) and so forth. The embodiment is exemplified as being 0.75 inches inside diameter, 0.75 inches long and preferably made of plastic, in particular PVC, although any desired material may be utilized. The ring configuration provides good stability and skin contact for the EDR, PPG, temperature sensors, but is limited in its ability to accommodate different finger sizes. A large diameter ring with different sized inserts is one solution, or a range of ring sizes could be made to accommodate a range of finger sizes.

Figures 7A, 7B:
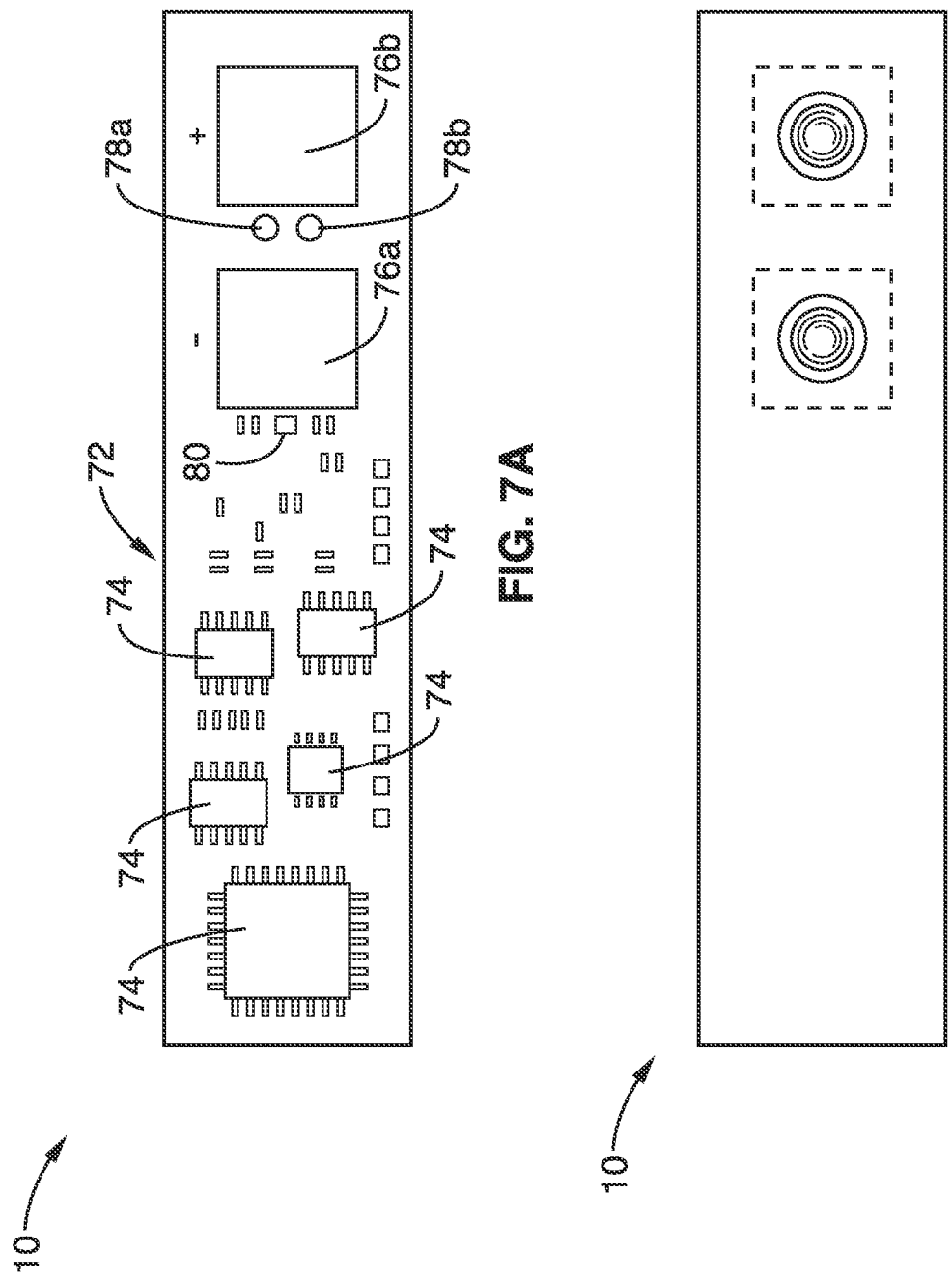
FIG. 7A and FIG. 7B are renditions of the biometric sensor array circuit board of FIG. 2, shown aside a dual contact element for overlaying the circuit board.

FIG. 7A and FIG. 7B illustrate an example embodiment of a dual electrode surface geometry, seen in FIG. 7B in relation to the biometric sensor circuit board seen here in FIG. 7A. An innovation in the functioning of the EDR sensor is provided herein in the form of the partial vacuum (PV) electrode to finger contact. The PV is achieved by creating a slightly concave surface of the electrode that contacts the skin. The well of this cavity having a relatively smooth shape to which the skin of the finger readily conforms. By applying a small pressure to the electrode to skin interface, the elasticity of the skin fills the concavity and is held in place by partial vacuum. This principle applies to most forms of cavities or depressions on the electrode surface that fit on the axial surface of the finger, thus these cavities should be approximately 0.125 inches to 0.25 inches in diameter. In FIG. 7B, the pair of EDR electrodes are seen with a central concave well of 0.067 inch depth. The previously described sensor board with flat electrodes is shown for size comparison.

The PV electrode in conjunction with the previously described enclosure or ring significantly enhances the functionality of the sensor and allows more use cases that involve active hand motion. Circuit board fabrication may incorporate surface features, such as removal or additive methods (e.g., drilling, grinding, building up, and so forth) into or alternatively onto the surface of the board. The cavity area is preferably coated with a highly conductive metal or alloy that has low oxidation potential, such as gold electroplating.

There are many cavity patterns that can be configured in, or on, a PCB and then plated to produce a functional EDR electrode set. One alternative embodiment utilizes multiple cavity areas for each electrode, such as an array of micro wells (e.g., a diameter of approximately 1 mm or larger) in an area, (e.g., a square or circle of 0.50 inch diameter) that improves accuracy when performing select measurements.

FIG. 8A through FIG. 8C illustrate different example embodiments 150*a*, 150*b*, 150*c*, of electrode pairs for use with the biometric sensor circuit. Flat sensor areas 152 in FIG. 8A are shown in comparison with the PV cupped sensors 154, 156 of FIG. 8B and FIG. 8C. Embodiment 154 has the sensor pads themselves being cupped while embodiment 156 has the sensor pads within a cupped sensor area. It should also be noted that embodiments 152, 154 are shown with the sensor area in a lower level of the structure, with a recessed sensor area 158, while embodiment 156 has sensors retained in a flat region.

2. Software Description 2.1 Introduction

The biometric sensor array is configured to send sensor data to the mobile device, such as through the exemplified audio interface or wireless interface. The data stream from the biometric sensor array is (a) decoded in the mobile device, (b) displayed in raw data form (e.g., graphing routine), (c) processed to derive averaged or time related values, and (d) displayed in the form of animation. It should be appreciated that the decoding includes decoding from the frequency division multiplexed format, and putting the signal in a format, including any desired scaling or offset, to simplify data display and any calculations performed interoperatively on the data signals as a whole. These software routines are executed on the processor of the mobile device.

2.2 Raw Data and Derived Data

Raw data can be derived and displayed from multiple sensor feedback channels, such as seven channels, in the current embodiment of the biometric sensor. These seven channels comprise: (1) EDR tonic, (2) EDR phasic, (3) Infrared (IR) reflection (cardiac pulse), (4) Skin temperature, (5) Acceleration in X direction, (6) Acceleration in Y direction, (7) Acceleration in Z direction.

Additional information is provided in response to calculations performed on the raw data. This information is particularly useful for interactive applications executing according to the present invention, which utilize combinations of emotion-related biometric information and acceleration within the biometric sensor. The current embodiment derives emotion metrics which include heart rate (HR), heart rate variability (HRV), and respiration rate based on HRV, as well as activity information on an acceleration sensor.

Accelerations sensed by the acceleration sensor are utilized for motion correcting information from other sensors, most beneficially the EDR and/or PPG sense data. The present embodiment provides two modes of biometric sensor artifact rejection. Both modes utilize temporal correlation between the signal to the corrected and the accelerometer signal. It will be noted that the signals to be corrected are low frequency signals (e.g., EDR is in the range from 0.25 Hz to 5 Hz), while the motion artifacts contain higher frequency content, such as at and above approximately 20 Hz to 100 Hz.

By way of example and not limitation, the following exemplifies correcting the EDR and PPG signal. In the first mode the EDR and PPG data is rejected in response to sensing a sufficient acceleration (e.g., exceeding a motion threshold) from the acceleration sensor, thus eliminating the section of signal containing the motion artifact. This mode can also preferably verify that the EDR and/or PPG data signal contains high frequency content prior to eliminating that section of the signal being registered. The program simply shuts off EDR and PPG channel data when a high frequency EDR signal input comes at the same time as a sufficient acceleration is sensed in either X, Y, or Z directions to cross a desired amplitude threshold. This may be performed, by way of example, by electrically blocking the signal or removing representative data entries from a buffer. The interrupt in the EDR and PPG signals only lasts as long as the motion artifact, whereby the output signals are restored when either acceleration or high frequency EDR and/or PPG signals return to their normal low frequency nature.

In the second mode, a form of noise cancelation is provided. This noise cancelation form of correction requires more processing overhead than the first mode of correction. In response to receiving a sufficient acceleration (e.g., exceeding a motion threshold), and preferably also detecting a high frequency component in the EDR and/or PPG signal, then a compensation signal representing the motion artifact is subtracted from the EDR and/or PPG signals. The compensation signal can be determined from the acceleration signals, or from the high-frequency components of the EDR or PPG signal being corrected, or more preferably to a combination of acceleration and EDR/PPG signals. As a result of this form of cancelation, only the motion artifact is removed from the corrected EDR and/or PPG signals. In one embodiment, the compensation signal is generated on a parallel channel and has a component which is 180 degrees out of phase with the motion artifact contained in the EDR and/or PPG signal. The generated EDR and/or PPG signal is then combined with the compensation signal to generate a corrected EDR and/or PPG signal without the motion artifacts.

It should be appreciated that the above modes of motion artifact cancelation can be performed by programming executing on the processor of the biometric sensor array, or by programming executing on the processor of the mobile device. In at least one embodiment, the first mode can be selectively performed on the processor of the sensor array, while the second mode is alternatively performed on the processor of the mobile device.

Figure 9A:
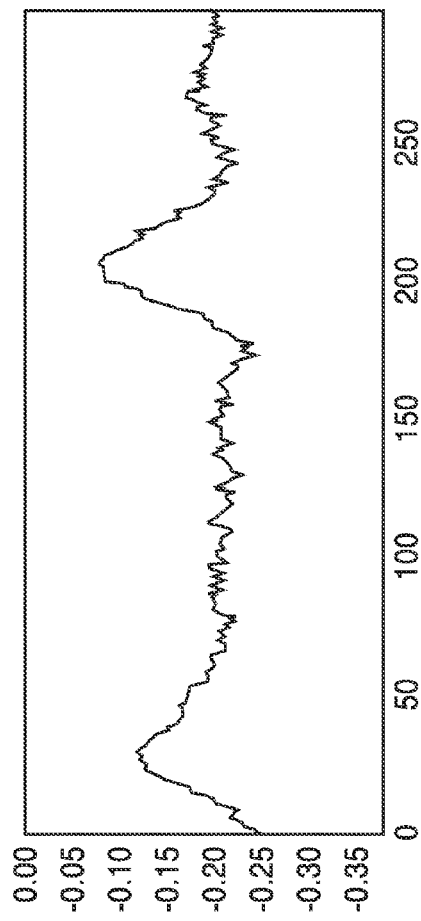
FIG. 9A is a plot of phasic EDR according to an embodiment of the present invention.
Figure 9B:
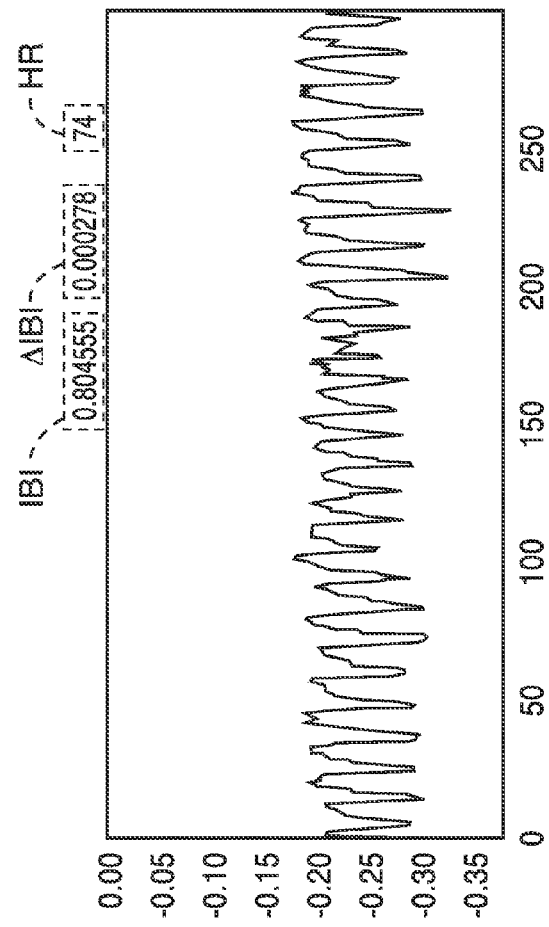
FIG. 9B is a plot of cardiac pulse deflections according to an embodiment of the present invention.

FIGS. 9A and 9B illustrate example screens from the current embodiment. In FIG. 9A is shown phasic EDR including two upward deflections caused by decreased skin resistance in response to sharp inhalation. The plot of FIG. 9B shows cardiac pulse deflections corresponding to IR light scattered by blood perfusion in the finger. Heart rate is derived by timing the peaks in the pulse plot as shown by the small number on the right with value "74" marked HR. Heart rate variability is calculated as the change in HR over a given set of heart beats. In this case a moving set of four beats is used to make a calculation of the change in HR. The inter-beat interval (IBI) is shown by the number on the left side marked as IBI, and the change in IBI is shown by the number in the middle marked as Δ IBI. The clinical standard for calculating HRV is over a period of five minutes with the subject lying quietly for the entire time of the evaluation. So in calculating HRV, it is useful to record the time interval used for the data recording.

Figure 10:
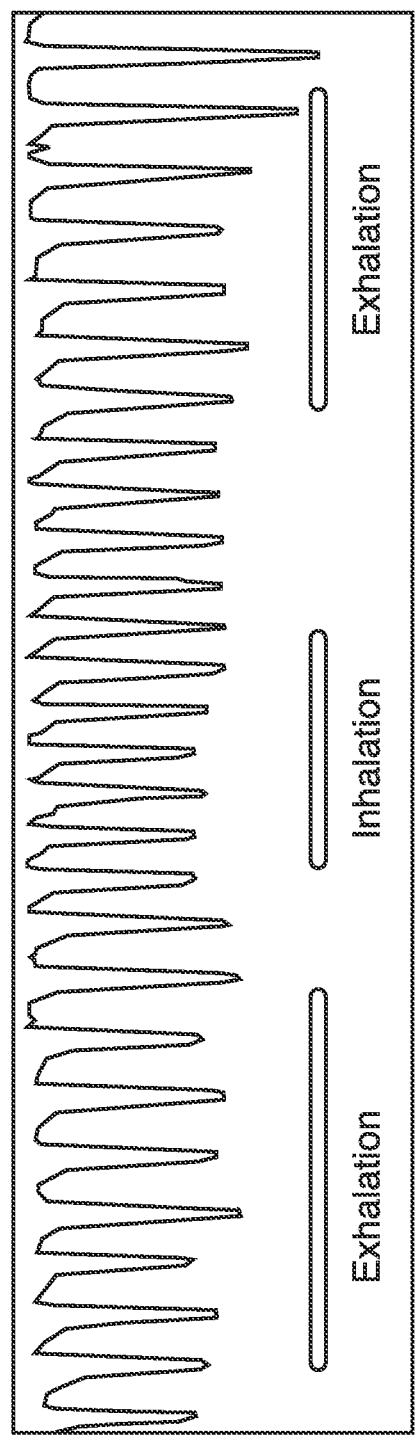
FIG. 10 is a graph of heart rate variability over exhalation and inhalation periods, according to an embodiment of the present invention.

FIG. 10 shows heart rate variability with exhalation and inhalation periods shown displayed over the graph. Table 1 shows derived data and data correlations. It is seen in this table that HRV is generated in response to the standard deviation of HR over time (e.g., measured in seconds or heart beats), while respiration rate is determined from analyzing HRV over time.

2.3 Data Flow for Real-Time Applications on Mobile Device

FIG. 11 illustrates an embodiment of a method for connecting the biometric sensor array to a mobile device using the audio port for collecting biofeedback data processed on the mobile device. In step 170 the biometric sensor array is connected to the microphone (mic) input of a mobile device. The user then activates, or has previously activated, the application (app) 172 on the mobile device. User then selects to start the data capture (audio capture) 174 in the application. The audio is exemplified as being captured using the callback method 176, this is performed by determining the period of the incoming signal, the values is put in one of two buffers, and the average of the two buffers is maintained periodically. The average values are determined and graphed in step 178, with the graph being periodically refreshed in step 180. It should be noted that the steps 170, 172, 174 involve the user interaction with the hardware and application, while steps 176, 178 and 180 are performed by the application program executing on the mobile device in conjunction with biometric sensor array of the invention. It should be noted that the embodiment shown provides two simultaneous data channels on the audio connection, while the hardware can be configured, such as using a wireless communication protocol, to provide any desired number of data channels from which the application can log, derive, calculate values on this data in separate channels or more particularly, in response to interoperable data utilization. One of ordinary skill in the art will appreciate that the method steps of FIG. 11 are substantially applicable to the alternate use of a wireless communication port that is activated for communication with the biometric sensitive application executing on the mobile device.

2.4 Interactive Applications and Use Scenarios

The raw and derived data of user biometrics captured by the biometric sensor hardware can be utilized in a variety of ways according to the invention within interactive applications (apps) on the mobile device. Each of these applications interoperably utilizes information from multiple sensors upon which to base decisions. As a first example, the sensed accelerations in the X, Y and Z directions are utilized in a process of motion artifact removal from the data received from the other channels, as previously described. As a second example, many of the applications utilize a weighted sum of the phasic EDR and HRV to determine an overall state measure. The weighting of the sum, that is its relative contributions and scaling, have been determined from extensive amounts of data collected.

The present invention provides a number of general application areas which beneficially allow a user to determine good stress from bad stress, detect short term and long term stress, and otherwise determine the biometrics of user emotional state in response to stimuli and as a basis for, or as one parameter of numerous parameters, within other applications and games.

The next section summarizes a number of example applications relying on novel elements of the present invention. By way of example and not limitation, these applications include a lie detector game, meditation challenge, hot or not reaction capture, daily stress, good versus bad stress, chronic stress, cool head, and focus groups. Table 2 shows data correlations and associated results for these example applications. It should be noted that thresholds for the results do not rely on predetermined values, such as from a table, but are based on relative changes over time. It is readily seen from this table that the present invention utilizes data from multiple sensors in determining a result for the application. The following provides additional details about these example applications.

(A) Lie Detector Game: The system is used to detect stress induced in response to questioning (e.g., verbal, or less preferably textual). The data from the EDR and PPG channels are processed together to give a phasic EDR response coupled with HR and short term HRV. Overall, detection of increased EDR while detecting decreases in HRV is the principle indicator of the induced stress of a lie. More particularly, after a question is posed, the basic algorithm is: (1) Increased EDR+ increased HR+decreased HRV="lie" (induced stress). (2) Steady EDR+steady HR+increased HRV="truth". (3) Decreased EDR+lower HR +increased HRV="truth". (4) Increased EDR+steady HR+decreased HRV="lie". So it view of the above it is seen that increased EDR and decreased HRV are the main indicators of lie induced stress. These interoperative determinations are summarized in Table 2. The general game environment is with a small group of people with one user wearing the sensor. The user stress response can be viewed on a display from one mobile device (such as a tablet), or the user response can be sent via internet to multiple devices creating an event for viewers in remote locations. Simply using a graphical display is sufficient to engage the group questioning the user, and many other forms of response display are possible using animation driven by the EDR and HR signals.

(B) Meditation Challenge: An Internet based interactive game wherein multiple users (two or more) use the biofeedback information provided to intentionally reduce their stress levels at a specific time based on a challenge placed among the users. This application uses phasic and tonic EDR, short term HRV, and temperature. The object is to reduce stress levels at a particular time for a given interval, such as "at 10 AM take 10 minutes" and reduce your levels. Based on the displayed information the user attempts to reduce tonic EDR plot and minimize fluctuations in the phasic EDR plot. At the same time the aim is to increase HRV (a healthy sign) over the challenge period, and increase your hand temperature. The general object in this application is to display sensor information and information derived from correlating data from multiple sensors, to the user. The user can then direct their attention toward changing their emotional state as reflected by the displayed information. In a simple example, the display may show an EDR plot, whereby the user meditates on bringing this value lower and lower on the graph. Similarly, HRV is displayed and the user works toward increasing HRV by taking deeper slower breaths. More particularly, multiple elements are displayed, and/or a combined display is output.

In at least one embodiment of the invention, the system marks displayed graphical results (for this and other applications according to the invention), such as with the graph color as it is plotted, in response to the system sensing a changing trend line. For example, with both EDR and HRV being displayed, as the user breathes more deeply, the new plot of HRV is highlighted, such as in green to indicate a positive change, thus making it easier for the user to discern positive changes in a given parameter. Conversely, in the example above, if user breathing is shorter and shallower, then the plot would be differently highlighted, such as changing from its default color to increasing shades of red. The data from each user is displayed on each participants' mobile device.

In this meditation challenge application each user is not preferably competing based on their scores, but rather toward making improvements over their personal bests previously achieved. In at least one embodiment, the application contemplates allowing at least one user to act as a coach to aid one or more other participants in effecting a positive physiological change.

(C) "Hot or Not": Reaction to various images or comments are scored using phasic EDR and HR. The speed of the phasic EDR signal is ideal for determining reactions to stimuli. It should be noted that both what users react to, and what they do not react to, is interesting and can be entertaining. In at least one embodiment, multiple users over the internet participate in this reaction application. In one mode of the application, the stimuli given to the users is generated by the system, while in another mode users generate the stimuli.

In at least one embodiment, in response to detecting a sufficient emotional reaction, the programming operates to trigger camera activation on the mobile device (i.e., cell phones and other mobile devices typically contain cameras), in either still or video mode as desired, whereby a picture, or short video snippet of 1-4 seconds, is captured of the user and their immediate emotional reaction. In one mode of the invention, the programming shares these photos/videos with the other participants. The camera feature described above is applicable to the Hot or Not application as well as other applications of the present invention.

(D) Daily Stress: This application provides user feedback that can help promote improved health and wellness by giving data about autonomic responses to everyday stimuli. This application utilizes phasic and tonic EDR, longer term HRV, activity indicators based on accelerometer data, and a microphone input to synchronize the data to environmental activity.

(E) Good versus Bad Stress: This application allows the user to determine their levels of "good stress" versus "bad stress". It is understood that certain forms of stress, such as during mild exercise in which pulse rate and breathing increase along with concomitant stress factors, are beneficial. However, "bad stress" arises when the body appears subjected to stress, (e.g., fight or flight response), but is not performing physical activity, such as when a person becomes frustrated while working at the computer. The bad stress can be sensed by increased EDR, HR, with decreased HRV due to shallow breathing.

(F) Chronic Stress: This application is a tracking application that records longer term responses. Since the finger probe is comfortable and allows unencumbered finger motion the stress levels may be recorded over the long term, and/or data collected at more frequent intervals. This application uses tonic EDR, HR, longer term HRV, and temperature. The object is for the user to lower EDR and increase HRV, and try to avoid stress induced increases in HR. In at least one embodiment, each channel can be plotted separately so the user can review the data at the end of the day. In at least one mode the system provides a logging function which allows users to make notes about activity during the day.

(G) Cool Head: This application provides an interactive game, in which the emotional state of the gamer is incorporated into game play. The object is to keep cool and unexcited to advance to higher levels of game play. For instance, in virtual auto racing, points are awarded or higher speed is possible for staying calm. This application uses phasic EDR, HR, and accelerometers to monitor unnecessary motion. This is similar to the lie detector whereby the user tries not to react to stimulation. The application logs game events and monitors user reaction to those events. The user loses points if they respond to the event, such as evidenced by an increase in EDR and HR. Points are scored for keeping EDR steady and more points scored for decreased EDR. Points are lost for increased HR and accelerometer activity. Points are scored for decreased HR and acceleration activity.

(H) Focus Groups: In this application, users are monitored in a controlled environment to determine the most effective form of advertising or attention getting stimuli. Phasic EDR and HR give real-time feedback as users react to presentation material. Since advertisers are looking for "engagement" and an emotional reaction from a consumer, the app would monitor user reaction during and after the display of an image or video clip. An increase in the EDR and HR indicate user arousal and positive reaction to the content. A steady or decreased EDR and HR would indicate a neutral or disinterested user reaction.

2.5 Coding Examples

Processing of data from the biometric sensor array is performed by application programming executing in the mobile device to which the biometric sensor array is attached, or otherwise has communication connectivity. The following are provided by way of example, and not limitation, of that programming.

Table 3 provides an example embodiment for gathering EDR data and displaying a plot of EDR with respect to time.

Table 4 provides an example embodiment for finding heart rate (HR) of a preprocessed PPG output, determining a confidence measure, and performing graphing functions.

Embodiments of the present invention may be described with reference to flowchart illustrations of methods and systems according to embodiments of the invention, and/or algorithms, formulae, or other computational depictions, which may also be implemented as computer program products. In this regard, each block or step of a flowchart, and combinations of blocks (and/or steps) in a flowchart, algorithm, formula, or computational depiction can be implemented by various means, such as hardware, firmware, and/or software including one or more computer program instructions embodied in computer-readable program code logic. As will be appreciated, any such computer program instructions may be loaded onto a computer, including without limitation a general purpose computer or special purpose computer, or other programmable processing apparatus to produce a machine, such that the computer program instructions which execute on the computer or other programmable processing apparatus create means for implementing the functions specified in the block(s) of the flowchart(s).

Accordingly, blocks of the flowcharts, algorithms, formulae, or computational depictions support combinations of means for performing the specified functions, combinations of steps for performing the specified functions, and computer program instructions, such as embodied in computer-readable program code logic means, for performing the specified functions. It will also be understood that each block of the flowchart illustrations, algorithms, formulae, or computational depictions and combinations thereof described herein, can be implemented by special purpose hardware-based computer systems which perform the specified functions or steps, or combinations of special purpose hardware and computer-readable program code logic means.

Furthermore, these computer program instructions, such as embodied in computer-readable program code logic, may also be stored in a computer-readable memory that can direct a computer or other programmable processing apparatus to function in a particular manner, such that the instructions stored in the computer-readable memory produce an article of manufacture including instruction means which implement the function specified in the block(s) of the flowchart(s). The computer program instructions may also be loaded onto a computer or other programmable processing apparatus to cause a series of operational steps to be performed on the computer or other programmable processing apparatus to produce a computer-implemented process such that the instructions which execute on the computer or other programmable processing apparatus provide steps for implementing the functions specified in the block(s) of the flowchart(s), algorithm(s), formula(e), or computational depiction(s).

From the discussion above it will be appreciated that the invention can be embodied in various ways, including the following:

1. An apparatus for estimating emotional state of a user for display on a mobile device, said apparatus comprising (a) a housing configured for retention of a finger of a user; (b) a sensor circuit retained in said housing; (c) said sensor circuit comprising a plurality of sensors configured for skin contact with a portion of the finger of the user; (d) said plurality of sensors comprising electrodermal response (EDR), photoplethysmograph (PPG), temperature, and acceleration sensors; (e) said sensor circuit comprising a communications interface configured for communicating data from said sensors to a mobile device; (f) said sensor circuit comprising a processor and programming executable on said processor for receiving input data from said sensors, processing said input data, and outputting processed data to the mobile device through said communications interface; (g) wherein the mobile device is configured for hosting an application program for communicating with said processor, post-processing said processed data, and displaying said post-processed data as biofeedback data.

2. The apparatus of any of the previous embodiments, wherein said acceleration sensor comprises a three axis acceleration sensor configured for sensing acceleration in the X, Y and Z directions.

3. The apparatus of any of the previous embodiments, wherein said EDR sensor generates a tonic signal and a phasic signal as an indication of arousal and mood.

4. The apparatus of any of the previous embodiments, wherein said PPG sensor measures user cardiac pulse from which heart rate (HR) and heart rate variability (HRV) can be determined.

5. The apparatus of any of the previous embodiments, wherein said communications interface comprises an audio frequency electronic signal interface configured for connection to a microphone input of the mobile device.

6. The apparatus of any of the previous embodiments, wherein said audio frequency electronic signal interface utilizes amplitude modulation and frequency division multiplexing of multiple signals from said sensors.

7. The apparatus of any of the previous embodiments, wherein said communications interface comprises a wireless signal interface.

8. The apparatus of any of the previous embodiments, wherein said wireless signal interface comprises a Bluetooth interface.

9. The apparatus of any of the previous embodiments, wherein said finger has knuckles, said finger has a fingertip, and said fingertip has a pad; and wherein said housing is configured for retention on the fingertip with said EDR, PPG and temperature sensors held against the pad of the fingertip; or wherein said housing is configured as a ring for retention between the knuckles of a finger with said EDR, PPG and temperature sensors held against the pad of the finger between the knuckles.

10. A system for estimating emotional state of a user for display on a mobile device, said apparatus comprising (a) a housing configured for retention of a finger of a user; (b) a sensor circuit retained in said housing; (c) said sensor circuit comprising a plurality of sensors configured for skin contact with a portion of the finger of the user; (d) said plurality of sensors comprising electrodermal response (EDR), photoplethysmograph (PPG), temperature, and acceleration sensors; (e) said sensor circuit comprising a communications interface configured for communicating data from said sensors to a mobile device; (f) said sensor circuit comprising a processor and programming executable on the processor for receiving input data from said sensors, processing said input data, and outputting processed data to the mobile device through said communications interface; and (g) an application program configured for execution on a processor of a mobile device having a display and user inputs and which is configured to receive said processed data; (h) said application program configured for communicating with said sensor circuit processor, post-processing said processed data, and displaying said post-processed data on said display as biofeedback data.

11. The system of any of the previous embodiments, wherein said application program performs motion artifact removal on EDR and PPG signals in response to acceleration sensed by said acceleration sensor.

12. The system of any of the previous embodiments, wherein said sensor array further comprises a temperature sensor.

13. The system of any of the previous embodiments, wherein said application program is further configured for performing a weighted average of said EDR and PPG sensors to create an overall emotional state estimation.

14. The system of any of the previous embodiments, wherein said EDR sensor generates a tonic signal and a phasic signal as an indication of arousal and mood.

15. The system of any of the previous embodiments, wherein said PPG sensor measures user cardiac pulse from which heart rate (HR) and heart rate variability (HRV) can be determined.

16. The system of any of the previous embodiments, wherein said acceleration sensor comprises a three axis acceleration sensor configured for sensing acceleration in the X, Y and Z directions.

17. The system of any of the previous embodiments, wherein said communications interface comprises an audio frequency electronic signal interface from said apparatus configured for connection to a microphone input of a mobile device.

18. The system of any of the previous embodiments, wherein said communications interface comprises a wireless signal interface.

19. The system of any of the previous embodiments, wherein said application program is configured to detect good stress versus bad stress for the user.

20. The system of any of the previous embodiments, wherein said application program is configured to detect user short term and long term stress.

21. The system of any of the previous embodiments, wherein said application program is configured to detect user emotional state as a basis for results and decisions in game scenarios.

22. The system of any of the previous embodiments, wherein said application program is configured to detect user emotional state in response to specific stimuli.

23. A system for estimating emotional state of a user for display on a mobile device, said apparatus comprising (a) a mobile device having a processor, a display, and a user interface; (b) a sensor array configured for communication with said mobile device; (c) a housing of said sensor array configured for retention of a finger of a user; (d) a sensor circuit retained in said housing; (e) said sensor circuit comprising a plurality of sensors configured for skin contact with a portion of the finger of the user; (f) said plurality of sensors comprising electrodermal response (EDR), photoplethysmograph (PPG), temperature, and acceleration sensors; (g) said sensor circuit comprising a communications interface configured for communicating data from said sensors to the mobile device; (h) said sensor circuit comprising a processor and programming executable on said processor for receiving input data from said sensors, processing said input data, and outputting processed data to said mobile device through said communications interface; (i) said mobile device having a communications interface configured for communication of data with said sensor circuit; and (j) an application program configured for execution on the processor of said mobile device; (k) said application program configured for communicating with said sensor circuit processor, post-processing said processed data, and displaying said post-processed data on said display as biofeedback data.

24. A system for displaying good stress versus bad stress on a mobile device in response to biofeedback signals received from an sensor array, said system comprising: (a) a sensor array; (b) a housing for said sensor array which is configured for insertion and retention of a finger of a user; (c) a sensor circuit retained in said housing; (d) said sensor circuit comprising a plurality of sensors configured for skin contact with a portion of the finger of the user; (e) said plurality of sensors comprising electrodermal response (EDR), photoplethysmograph (PPG), and acceleration sensors; (f) said sensor circuit comprising a communications interface configured for communicating said data from said sensors to a mobile device; (g) said sensor circuit comprising a processor and programming executable on the processor for receiving input data from said sensors, processing said input data, and outputting processed data on to the mobile device through said communications interface; and (h) an application program configured for execution on a processor of a mobile device having a display and user inputs configured to receive said processed data; (i) said application program configured for communicating with said sensor circuit processor, post-processing said processed data, performing motion artifact removal on EDR and PPG signals in response to accelerations sensed by said acceleration sensor, combining EDR and PPG signals using a weighted average to create an overall emotional state estimation, and determining and displaying good stress versus bad stress for the user.

Although the description above contains many details, these should not be construed as limiting the scope of the invention but as merely providing illustrations of some of the presently preferred embodiments of this invention. There-fore, it will be appreciated that the scope of the present invention fully encompasses other embodiments which may become obvious to those skilled in the art, and that the scope of the present invention is accordingly to be limited by nothing other than the appended claims, in which reference to an element in the singular is not intended to mean "one and only one" unless explicitly so stated, but rather "one or more." All structural, chemical, and functional equivalents to the elements of the above-described preferred embodiment that are known to those of ordinary skill in the art are expressly incorporated herein by reference and are intended to be encompassed by the present claims. Moreover, it is not necessary for a device or method to address each and every problem sought to be solved by the present invention, for it to be encompassed by the present claims. Furthermore, no element, component, or method step in the present disclosure is intended to be dedicated to the public regardless of whether the element, component, or method step is explicitly recited in the claims. No claim element herein is to be construed under the provisions of 35 U.S.C. 112, sixth paragraph, unless the element is expressly recited using the phrase "means for."

TABLE 1

Derived Data and Data Correlations

| Derived data | Method of generation |
|---|---|
| HRV | Standard Deviation of HR over X seconds = HR variability over set of X heart beats, where X is determined by the user |
| Respiration rate | Plot HRV vs. time |

TABLE 2

Data Correlations and Result (output) for Sample Applications

| Use case | EDR | HR | HRV | Resp | Temp | Accel | RESULT |
|---|---|---|---|---|---|---|---|
| Lie Det. | If + | If + | If − | If + | | If + | lie |
| Lie Det. | If o | If o | If o | If o | | If o | truth |
| Lie Det. | If − | If o | If o | If o | | If o | truth |
| Lie Det. | If o | If + | If − | If + | | If o | lie |
| Med Chal | If − | If − | If + | If − | If + | If o | win |
| Med Chal | If + | If + | If − | If + | If − | If o | lose |
| Med Chal | If − | If o | If o | If o | If o | If o | win |
| Med Chal | If + | If o | If − | If + | If − | If + | lose |
| Hot or Not | If + | If + | If o | If + | | | hot |
| Hot or Not | If o | If o | If o | If o | | | not |
| Hot or Not | If − | If o | If o | If − | | | not |
| Hot or Not | If + | If o | If o | If o | | | hot |
| Healthy Stress | If + | If + | If + | If + | If + | | good |
| Unhealthy Stress | If + | If + | If − | If − | If − | | bad |
| Cool Head | If o | If o | If o | If o | | | win |
| Cool Head | If − | If o | If + | If − | | | win |
| Cool Head | If + | If + | If o | If o | | | lose |

TABLE 2-continued

Data Correlations and Result (output) for Sample Applications

| Use case | EDR | HR | HRV | Resp | Temp | Accel | RESULT |
|---|---|---|---|---|---|---|---|
| Cool Head | If + | If + | If − | If + | | | lose |
| Focus Gr. | If + | If + | If o | If + | If + | | big win |
| Focus Gr. | If + | If o | If o | If o | If o | | win |
| Focus Gr. | If o | If + | If o | If + | If o | | OK |
| Focus Gr. | If − | If o | If o | If o | If o | | loser |

("+" = increase "−" = decrease "o" = no change)

TABLE 3

Sample EDR Generation Code

```
% Gather Raw EDR Data and Plot EDR voltage vs time
% Input data
[fn, pn] = uigetfile('*.dat', ['Choose first data file to be
analyzed.']);
path = [pn fn];
fp = fopen(path,'rt');
% check to make sure file was opened successfully
if fp == −1
    error(['Unable to open ' path '.']);
end
BioDataRaw1 = fscanf(fp,'%g', [1 inf]);
status = fclose(fp);
% Plot Data Raw EDR
NumSamples = length(BioDataRaw1)−1;
time = (0:(NumSamples))/100;
plot(time,BioDataRaw1)
edrSampleRate(1/time)
edrRawData(BioDataRaw1)
load c:\ben\senstream\projects\0.5to12Bandpass.mat
alpha = filter(Num,1, BioDataRaw1);
NumSamples = length(alpha)−1;
time = (0:(NumSamples))/100;
plot(time,EDR)
xlabel('Time (sec)')
Allpass = zeros(1,length(Num));
Allpass((length(Num)−1)/2) = 1;
load c:\ben\senstream\projects\10HzLPF.mat
edr = abs(alpha);
edr = filter(Num,1, alpha);
load c:\ben\senstream\projects\20HzLPF.mat
nonedr = filter(Allpass,1, BioDataRaw1);
nonedr = abs(nonedr);
nonedr = filter(Num,1, nonedr);
ratio = edr./nonedr;
ratio = ratio.*ratio;
ratio(1:length(Allpass))=0;
NumSamples = length(ratio)−1;
time = (0:(NumSamples))/100;
plot(time,ratio)
EDRSampleRate(1/time)
EDR(ratio)
```

TABLE 4

Sample HR Generation Code

```
% findHR
% This script finds the heart rate of a pre-processed PPG output −
%   i.e. from the peak voltage of IR detector output.
function [hrFinal,finalFrames] = findHR(preprocPPG, plotOpt);
if nargin < 2
    plotOpt = 'false';
    if nargin < 1
        error('Must supply pre-processed PPG.');
    end
end
STD_MULT = 3; % threshold is intially set to this number of standard deviations.
SLOPE = 0.4; % threshold decreased by this much in one period of heart.
STARTING_HR = 60; % bpm
```

TABLE 4-continued

Sample HR Generation Code

```
CAL_LENGTH = 3; % The amount of time that the std is calculated over in seconds.
CAL_BEATS = 3; % the number of beats that are used for calibration.
FRAME_RATE = 500; % sample rate of preprocEKG;
PAUSE_TIME = 0.3; % a period of time in seconds after a beat where no new beats
can be found.
MIN_HR = 60; % minimum HR in BPM
MAX_HR = 150; % maximum HR
MAX_HR_CHANGE = 0.3; % 0.3
MEDFILT_LENGTH = 30; % length of median filter
MAX_BEAT_INC_RATIO = 0.5; % the maximum amount that the threshold can increase
when there is a new beat.
signal = preprocPPG;
% check to make sure that signal is at least CAL_LENGTH seconds long;
if length(signal)./FRAME_RATE < CAL_LENGTH
      error(['Input data must be at least ' num2str(CAL_LENGTH) ' seconds long.']);
end
% calculate starting threshold
thresh = STD_MULT.*std(signal([1:FRAME_RATE.*CAL_LENGTH]));
% start looking for heartbeats
count = 1;
beats = [ ];
beats2 = [ ];
tempHR = STARTING_HR;
stageFlag = 1;
hr = [ ];
frames = [ ];
indBeatsHR = [ ];
indBeatsHRIndex = [ ];
sizeBeats = [ ];
lastBeat = thresh;
%loop through all frames, starting with first frame after calibration section
frame = FRAME_RATE.*CAL_LENGTH + 1;
while frame < length(signal) – CAL_BEATS
      % check for signal > threshold
      if signal(frame) > thresh & stageFlag == 1
            stageFlag = 2;
      elseif stageFlag == 2 & signal(frame) – signal(frame – 1) < 0 % find peak
greater than thresh
            % found a beat
            beats = [beats frame – 1]; % save beat index
            sizeBeats = [sizeBeats signal(frame–1)]; % save beat size
                  % set threshold equal to peak value. Conditional statement limits how
much peak value can
                  % increase each time a beat is found
                  if signal(beats(end))./lastBeat – 1 > MAX_BEAT_INC_RATIO
                        thresh = lastBeat.*(1+MAX_BEAT_INC_RATIO);
                  else
                        thresh = signal(beats(end));
                  end
                  lastBeat = thresh;
            if length(beats) > 2% calculate heartrate once you have at least 2 beats
                  tempHR = 60.*FRAME_RATE./(beats(end) – beats(end – 1));
                  hr = [hr tempHR];
                  frames = [frames frame]; % this stores the frames that correspond to
each heartrate.
                              % used for graphing
            end
            stageFlag = 3;
      elseif stageFlag == 3 & count < PAUSE_TIME.*FRAME_RATE
                  % this is a period of time where no new beats can be detected
            count = count + 1;
      elseif stageFlag == 3 & count >= PAUSE_TIME.*FRAME_RATE
            count = 1;
            stageFlag = 1;
      end
      % threshold is always decreasing
      thresh = thresh – tempHR.*SLOPE.*thresh./FRAME_RATE./60;
      % plot
      if(strcmp(plotOpt, 'true') & floor(frame./5) – frame./5 == 0)
            plot(timeAxis(frame), thresh, 'g.')
      end
% hr = [hr tempHR];
% increment frame
frame = frame + 1;
end
% clean up signal
hrClean = hr; % by the end of this block, hrClean has removed values outside the
acceptible range
```

TABLE 4-continued

Sample HR Generation Code

```
cleanFrames = frames;
greaterInd = (find(hrClean > MAX_HR));
lessthanInd = (find(hrClean < MIN_HR));
hrClean(greaterInd) = [ ];
cleanFrames(greaterInd) = [ ];
if((lessthanInd > 0) & (lessthanInd < length(hrClean)))
    hrClean(lessthanInd) = [ ];
    cleanFrames(lessthanInd) = [ ];
end
%hrClean = medfilt1(hrClean, MEDFILT_LENGTH);
confidence = zeros(size(hrClean));
hrFinal = hrClean;
% create confidence measure, simply std of recent heart rates
% also create final heartrate, which is a median filtered version of the clean
heart rate from above.
for i = MEDFILT_LENGTH:length(hrClean);
    confidence(i) = std(hrClean(i - MEDFILT_LENGTH + 1:i));
    hrFinal(i) = median(sort(hrClean(i - MEDFILT_LENGTH + 1:i)));
end
% these next lines make the graphs line up
% hrFinal(1:MEDFILT_LENGTH - 1) = [ ];
% confidence(1:MEDFILT_LENGTH - 1) = [ ];
% finalFrames = cleanFrames(MEDFILT_LENGTH:end);
finalFrames=cleanFrames;
PPGSampleRate(1/time)
PPGRawData(signal)
PulseEvent(beats)
PulseHeartRate(hr)
```

What is claimed is:

1. An apparatus for estimating emotional state of a user for display on a mobile device, said apparatus comprising:
(a) a housing configured for retention of a finger of a user;
(b) a sensor circuit retained in said housing;
(c) said sensor circuit comprising a plurality of sensors configured for skin contact with a portion of the finger of the user;
(d) said plurality of sensors comprising electrodermal response (EDR), photoplethysmograph (PPG), temperature, and acceleration sensors;
(e) said sensor circuit comprising a communications interface configured for communicating data from said sensors to a mobile device;
(f) said sensor circuit comprising a processor and programming executable on said processor for receiving input data from said sensors, processing said input data, and outputting processed data to the mobile device through said communications interface;
(g) wherein the mobile device is configured for hosting an application program for communicating with said processor, post-processing said processed data, and displaying said post-processed data as biofeedback data; and
(h) wherein said application program performs motion artifact removal on EDR and PPG signals in response to acceleration sensed by said acceleration sensor.

2. The apparatus recited in claim 1, wherein said acceleration sensor comprises a three axis acceleration sensor configured for sensing acceleration in the X, Y and Z directions.

3. The apparatus recited in claim 1, wherein said EDR sensor generates a tonic signal and a phasic signal as an indication of arousal and mood.

4. The apparatus recited in claim 1, wherein said PPG sensor measures user cardiac pulse from which heart rate (HR) and heart rate variability (HRV) can be determined.

5. The apparatus recited in claim 1, wherein said communications interface comprises an audio frequency electronic signal interface configured for connection to a microphone input of the mobile device.

6. The apparatus recited in claim 5, wherein said audio frequency electronic signal interface utilizes amplitude modulation and frequency division multiplexing of multiple signals from said sensors.

7. The apparatus recited in claim 1, wherein said communications interface comprises a wireless signal interface.

8. The apparatus recited in claim 7, wherein said wireless signal interface comprises a Bluetooth interface.

9. The apparatus recited in claim 1;
wherein said housing is configured for retention on a fingertip of a user with said EDR, PPG and temperature sensors held against a pad of the fingertip; or
wherein said housing is configured as a ring for retention between knuckles of a finger of a user with said EDR, PPG and temperature sensors held against the pad of the finger between the knuckles.

10. The apparatus as recited in claim 1, wherein said application program performs motion artifact removal on EDR and PPG signals in response to acceleration sensed by said acceleration sensor, by rejecting EDR and PPG data in response to sensing a sufficient acceleration from said acceleration sensor.

11. A system for estimating emotional state of a user for display on a mobile device, said apparatus comprising:
(a) a housing configured for retention of a finger of a user;
(b) a sensor circuit retained in said housing;
(c) said sensor circuit comprising a plurality of sensors configured for skin contact with a portion of the finger of the user;
(d) said plurality of sensors comprising electrodermal response (EDR), photoplethysmograph (PPG), temperature, and acceleration sensors;
(e) said sensor circuit comprising a communications interface configured for communicating data from said sensors to a mobile device;
(f) said sensor circuit comprising a processor and programming executable on the processor for receiving input data from said sensors, processing said input data, and outputting processed data to the mobile device through said communications interface; and (g) an application program configured for execution on a processor of a mobile device having a display and user inputs and which is configured to receive said processed data;

(h) said application program configured for communicating with said sensor circuit processor, post-processing said processed data, and displaying said post-processed data on said display as biofeedback data; and (i) wherein said application program further performs motion artifact removal on EDR and PPG signals in response to acceleration sensed as triaxial motion by said acceleration sensors in said sensor circuit configured for retention on the finger of the user for mediating motion effects which interfere with physiological signal measurements.

12. The system recited in claim 11, wherein said application program performs said motion artifact removal on EDR and PPG signals in response to acceleration sensed by said acceleration sensor, while also being configured for enabling a pointing function with appropriate finger motion, or gesture, as a user input.

13. The system recited in claim 11, wherein said sensor array further comprises a temperature sensor.

14. The system recited in claim 11, wherein said application program is further configured for performing a weighted average of said EDR and PPG sensors to create an overall emotional state estimation.

15. The system recited in claim 11, wherein said EDR sensor generates a tonic signal and a phasic signal as an indication of arousal and mood.

16. The system recited in claim 11, wherein said PPG sensor measures user cardiac pulse from which heart rate (HR) and heart rate variability (HRV) can be determined.

17. The system recited in claim 11, wherein said acceleration sensor comprises a three axis acceleration sensor configured for sensing acceleration in the X, Y and Z directions.

18. The system recited in claim 11, wherein said communications interface comprises an audio frequency electronic signal interface from said apparatus configured for connection to a microphone input of a mobile device.

19. The system recited in claim 11, wherein said communications interface comprises a wireless signal interface.

20. The system recited in claim 11, wherein said application program is configured to detect good stress versus bad stress for the user.

21. The system recited in claim 11, wherein said application program is configured to detect user short term and long term stress.

22. The system recited in claim 10, wherein said application program is configured to detect user emotional state as a basis for results and decisions in game scenarios.

23. The system recited in claim 11, wherein said application program is configured to detect user emotional state in response to specific stimuli.

24. The system as recited in claim 11, wherein said application program performs motion artifact removal on EDR and PPG signals in response to acceleration sensed by said acceleration sensor, by rejecting EDR and PPG data in response to sensing a sufficient acceleration from said acceleration sensor.

25. A system for estimating emotional state of a user for display on a mobile device, said apparatus comprising:

(a) a mobile device having a processor, a display, and a user interface;

(b) a sensor array configured for communication with said mobile device;

(c) a housing of said sensor array configured for retention of a finger of a user;

(d) a sensor circuit retained in said housing;

(e) said sensor circuit comprising a plurality of sensors configured for skin contact with a portion of the finger of the user;

(f) said plurality of sensors comprising electrodermal response (EDR), photoplethysmograph (PPG), temperature, and acceleration sensors, and wherein motion effects which interfere with physiological signal measurements of EDR and PPG captured at this finger sensing location of a user are mediated in response to utilizing acceleration data to compensate for any movement which arises at the finger location;

(g) said sensor circuit comprising a communications interface configured for communicating data from said sensors to the mobile device;

(h) said sensor circuit comprising a processor and programming executable on said processor for receiving input data from said sensors, processing said input data, and outputting processed data to said mobile device through said communications interface;

(i) said mobile device having a communications interface configured for communication of data with said sensor circuit; and (j) an application program configured for execution on the processor of said mobile device;

(k) said application program configured for communicating with said sensor circuit processor, post-processing said processed data, and displaying said post-processed data on said display as biofeedback data.

26. A system for displaying good stress versus bad stress on a mobile device in response to biofeedback signals received from an sensor array, said system comprising:

(a) a sensor array;

(b) a housing for said sensor array which is configured for insertion and retention of a finger of a user;

(c) a sensor circuit retained in said housing;

(d) said sensor circuit comprising a plurality of sensors configured for skin contact with a portion of the finger of the user;

(e) said plurality of sensors comprising electrodermal response (EDR), photoplethysmograph (PPG), and acceleration sensors;

(f) said sensor circuit comprising a communications interface configured for communicating said data from said sensors to a mobile device;

(g) said sensor circuit comprising a processor and programming executable on the processor for receiving input data from said sensors, processing said input data, and outputting processed data on to the mobile device through said communications interface; and (h) an application program configured for execution on a processor of a mobile device having a display and user inputs configured to receive said processed data;

(i) said application program configured for communicating with said sensor circuit processor, post-processing said processed data, performing motion artifact removal on EDR and PPG signals in response to accelerations sensed by said acceleration sensor, and combining EDR and PPG signals using a weighted average to create an overall emotional state estimation, and determining and displaying good stress versus bad stress for the user; and (j) wherein said application program is configured for processing said EDR and PPG signals in response to acceleration sensed as triaxial motion by said acceleration sensors in said sensor circuit configured for retention on the finger of the user for mediating motion effects which interfere with physiological signal measurements.

* * * * *